United States Patent
Cote et al.

(10) Patent No.: US 11,648,020 B2
(45) Date of Patent: May 16, 2023

(54) DEVICE AND METHOD FOR MANUAL ASPIRATION AND REMOVAL OF AN UNDESIRABLE MATERIAL

(71) Applicant: AngioDynamics, Inc., Latham, NY (US)

(72) Inventors: Seth Cote, Nashua, NH (US); Kevin Swift, Hudson, MA (US); James Culhane, Westborough, MA (US); James Mitchell, Ballston Spa, NY (US)

(73) Assignee: AngioDynamics, Inc., Latham, NY (US)

( * ) Notice: Subject to any disclaimer, the term of this patent is extended or adjusted under 35 U.S.C. 154(b) by 266 days.

(21) Appl. No.: 17/170,782

(22) Filed: Feb. 8, 2021

(65) Prior Publication Data
US 2021/0275199 A1 Sep. 9, 2021

Related U.S. Application Data

(60) Provisional application No. 62/971,280, filed on Feb. 7, 2020.

(51) Int. Cl.
*A61B 17/22* (2006.01)
*A61B 17/00* (2006.01)
*A61M 1/00* (2006.01)

(52) U.S. Cl.
CPC ........ *A61B 17/22* (2013.01); *A61B 17/00234* (2013.01); *A61M 1/74* (2021.05);
(Continued)

(58) Field of Classification Search
CPC .............. A61B 17/22; A61B 17/00234; A61B 17/22031; A61B 2017/00367;
(Continued)

(56) References Cited

U.S. PATENT DOCUMENTS

| | | |
|---|---|---|
| 3,831,587 A | 8/1974 | Boyd |
| 4,046,150 A | 9/1977 | Schwartz |
| 4,273,128 A | 6/1981 | Lary |
| 4,437,856 A | 3/1984 | Valli |
| 4,445,509 A | 5/1984 | Auth |

(Continued)

FOREIGN PATENT DOCUMENTS

| | | |
|---|---|---|
| AU | 2015274704 | 10/2016 |
| AU | 2016341439 | 5/2018 |

(Continued)

OTHER PUBLICATIONS

F.A.S.T. Funnel Catheter Proximal Occlusion Embolectomy/Thrombectomy System, Genesis Medical Interventional, 4 pages.

(Continued)

*Primary Examiner* — Shaun L David
*Assistant Examiner* — Rachael L Geiger
(74) *Attorney, Agent, or Firm* — DLA Piper LLP (US)

(57) ABSTRACT

The present invention is directed to a manually actuated aspiration device, aspiration system and a method of use to enable and facilitate en bloc removal of undesirable intravascular material, including, but not limited to, thrombus, embolus, or vegetation through a working lumen of a suction cannula during minimally invasive percutaneous procedures. The aspiration device includes valves oriented in opposite direction to control the fluid flow through the aspiration system and into a waste collection component. Alternatively, the aspiration system further comprises a filter that removes undesirable intravascular material prior to reinfusing blood into a patient's vasculature.

8 Claims, 17 Drawing Sheets

(52) U.S. Cl.
CPC ..... *A61M 1/76* (2021.05); *A61B 2017/00367* (2013.01); *A61B 2017/22079* (2013.01)

(58) Field of Classification Search
CPC .......... A61B 2017/00115; A61B 2017/00778; A61B 2017/22079; A61B 2017/0046; A61B 2017/308; A61B 2017/32007; A61B 2017/32008; A61B 2090/064; A61B 2217/005; A61B 10/0283; A61M 1/74; A61M 1/76
See application file for complete search history.

(56) References Cited

U.S. PATENT DOCUMENTS

| | | |
|---|---|---|
| 4,469,100 A | 9/1984 | Hardwick |
| 4,646,736 A | 3/1987 | Auth |
| 4,664,112 A | 5/1987 | Kensey |
| 4,671,796 A | 6/1987 | Groshong |
| 4,681,564 A | 7/1987 | Landreneau |
| 4,693,243 A | 9/1987 | Buras |
| 4,696,667 A | 9/1987 | Masch |
| 4,729,763 A | 3/1988 | Henrie |
| 4,747,821 A | 5/1988 | Kensey |
| 4,749,376 A | 6/1988 | Kensey |
| 4,790,812 A | 12/1988 | Hawkins, Jr. |
| 4,857,045 A | 8/1989 | Rydell |
| 4,857,046 A | 8/1989 | Stevens |
| 4,886,061 A | 12/1989 | Fischell |
| 4,895,166 A | 1/1990 | Farr |
| 4,895,560 A | 1/1990 | Papantonakos |
| 4,921,478 A | 5/1990 | Solano |
| 4,990,134 A | 2/1991 | Auth |
| 4,990,151 A | 2/1991 | Wallsten |
| 5,011,488 A | 4/1991 | Ginsburg |
| 5,019,089 A | 5/1991 | Farr |
| 5,030,201 A | 7/1991 | Palestrant |
| 5,074,841 A | 12/1991 | Ademovic |
| 5,084,052 A | 1/1992 | Jacobs |
| 5,092,839 A | 3/1992 | Kipperman |
| 5,092,877 A | 3/1992 | Pinchuk |
| 5,098,440 A | 3/1992 | Hillstead |
| 5,100,423 A | 3/1992 | Fearnot |
| 5,102,415 A | 4/1992 | Guenther |
| 5,114,399 A | 5/1992 | Kovalcheck |
| 5,115,816 A * | 5/1992 | Lee ................... A61M 5/1782 D24/146 |
| 5,158,533 A | 10/1992 | Strauss |
| 5,158,564 A | 10/1992 | Schnepp-Pesch |
| 5,188,618 A | 2/1993 | Thomas |
| 5,211,651 A | 5/1993 | Reger |
| 5,226,909 A | 7/1993 | Evans |
| 5,242,441 A | 9/1993 | Avitall |
| 5,257,974 A | 11/1993 | Cox |
| 5,273,526 A | 12/1993 | Dance |
| 5,306,250 A | 4/1994 | March |
| 5,334,208 A | 8/1994 | Soehendra |
| 5,423,799 A | 6/1995 | Shiu |
| 5,464,408 A | 11/1995 | Duc |
| 5,474,563 A | 12/1995 | Myler |
| 5,490,859 A | 2/1996 | Mische |
| 5,520,697 A | 5/1996 | Lindenberg |
| 5,540,707 A | 7/1996 | Ressemann |
| 5,569,275 A | 10/1996 | Kotula |
| 5,571,086 A | 11/1996 | Kaplan |
| 5,628,746 A | 5/1997 | Clayman |
| 5,632,755 A | 5/1997 | Nordgren |
| 5,643,309 A | 7/1997 | Myler |
| 5,653,684 A | 8/1997 | Laptewicz |
| 5,733,302 A | 3/1998 | Myler |
| 5,772,629 A | 6/1998 | Kaplan |
| 5,776,141 A | 7/1998 | Klein |
| 5,785,715 A | 7/1998 | Schatz |
| 5,800,457 A | 9/1998 | Gelbfish |
| 5,843,103 A | 12/1998 | Wulfman |
| 5,846,251 A | 12/1998 | Hart |
| 5,868,753 A | 2/1999 | Schatz |
| 5,873,882 A | 2/1999 | Straub |
| 5,908,435 A | 6/1999 | Samuels |
| 5,910,144 A | 6/1999 | Hayashi |
| 5,941,895 A | 8/1999 | Myler |
| 6,001,112 A | 12/1999 | Taylor |
| 6,059,745 A | 5/2000 | Gelbfish |
| 6,083,239 A | 7/2000 | Addis |
| 6,106,531 A | 8/2000 | Schatz |
| 6,159,220 A | 12/2000 | Gobron |
| 6,159,230 A | 12/2000 | Samuels |
| 6,161,547 A | 12/2000 | Barbut |
| 6,187,016 B1 | 2/2001 | Hedges |
| 6,203,537 B1 | 3/2001 | Adrian |
| 6,206,868 B1 | 3/2001 | Parodi |
| 6,206,898 B1 | 3/2001 | Honeycutt |
| 6,241,738 B1 | 6/2001 | Dereume |
| 6,280,413 B1 | 8/2001 | Clark |
| 6,280,464 B1 | 8/2001 | Hayashi |
| 6,283,940 B1 | 9/2001 | Mulholland |
| 6,287,321 B1 | 9/2001 | Jang |
| 6,364,896 B1 | 4/2002 | Addis |
| 6,394,978 B1 | 5/2002 | Boyle |
| 6,413,235 B1 | 7/2002 | Parodi |
| 6,423,032 B2 | 7/2002 | Parodi |
| 6,443,966 B1 | 9/2002 | Shiu |
| 6,451,036 B1 | 9/2002 | Heitzmann |
| 6,454,775 B1 | 9/2002 | Demarais |
| 6,454,779 B1 | 9/2002 | Taylor |
| 6,491,712 B1 | 12/2002 | O'Connor |
| 6,500,191 B2 | 12/2002 | Addis |
| 6,508,782 B1 | 1/2003 | Evans |
| 6,540,712 B1 | 4/2003 | Parodi |
| 6,547,754 B1 | 4/2003 | Evans |
| 6,569,181 B1 | 5/2003 | Burns |
| 6,582,396 B1 | 6/2003 | Parodi |
| 6,592,606 B2 | 7/2003 | Huter |
| 6,602,264 B1 | 8/2003 | Mcguckin, Jr. |
| 6,660,014 B2 | 12/2003 | Demarais |
| 6,666,874 B2 | 12/2003 | Heitzmann |
| 6,673,039 B1 | 1/2004 | Bridges |
| 6,676,692 B2 | 1/2004 | Rabkin |
| 6,679,893 B1 | 1/2004 | Tran |
| 6,685,722 B1 | 2/2004 | Rosenbluth |
| 6,695,858 B1 | 2/2004 | Dubrul |
| 6,702,830 B1 | 3/2004 | Demarais |
| 6,719,717 B1 | 4/2004 | Johnson |
| 6,749,619 B2 | 6/2004 | Ouriel |
| 6,802,846 B2 | 10/2004 | Hauschild |
| 6,808,520 B1 | 10/2004 | Fourkas |
| 6,808,531 B2 | 10/2004 | Lafontaine |
| 6,837,901 B2 | 1/2005 | Rabkin |
| 6,852,280 B2 | 2/2005 | Vijay |
| 6,878,153 B2 | 4/2005 | Linder |
| 6,905,490 B2 | 6/2005 | Parodi |
| 6,908,474 B2 | 6/2005 | Hogendijk |
| 6,936,060 B2 | 8/2005 | Hogendijk |
| 6,939,362 B2 | 9/2005 | Boyle |
| 6,945,977 B2 | 9/2005 | Demarais |
| 6,946,099 B2 | 9/2005 | Vijay |
| 6,960,222 B2 | 11/2005 | Vo |
| 6,962,598 B2 | 11/2005 | Linder |
| 7,014,913 B2 | 3/2006 | Pacetti |
| 7,063,707 B2 | 6/2006 | Bose |
| 7,108,704 B2 | 9/2006 | Trerotola |
| 7,118,585 B2 | 10/2006 | Addis |
| 7,153,292 B2 | 12/2006 | Morris |
| 7,153,320 B2 | 12/2006 | Euteneuer |
| 7,172,610 B2 | 2/2007 | Heitzmann |
| 7,175,660 B2 | 2/2007 | Cartledge |
| 7,220,269 B1 | 5/2007 | Ansel |
| 7,223,253 B2 | 5/2007 | Hogendijk |
| 7,229,402 B2 | 6/2007 | Diaz |
| 7,235,088 B2 | 6/2007 | Pintor |
| 7,258,696 B2 | 8/2007 | Rabkin |
| 7,300,458 B2 | 11/2007 | Henkes |
| 7,344,549 B2 | 3/2008 | Boyle |
| 7,351,255 B2 | 4/2008 | Andreas |

(56) References Cited

U.S. PATENT DOCUMENTS

| | | |
|---|---|---|
| 7,374,560 B2 | 5/2008 | Ressemann |
| 7,479,147 B2 | 1/2009 | Honeycutt |
| 7,655,016 B2 | 2/2010 | Demarais |
| 7,674,237 B2 | 3/2010 | O'Mahony |
| 7,678,130 B2 | 3/2010 | Mazzocchi |
| 7,682,563 B2 | 3/2010 | Carpenter |
| 7,713,227 B2 | 5/2010 | Wholey |
| 7,766,934 B2 | 8/2010 | Pal |
| 7,771,445 B2 | 8/2010 | Heitzmann |
| 7,771,452 B2 | 8/2010 | Pal |
| 7,776,062 B2 | 8/2010 | Besselink |
| 7,799,046 B2 | 9/2010 | White |
| 7,842,010 B2 | 11/2010 | Bonnette |
| 7,842,055 B2 | 11/2010 | Pintor |
| 7,862,575 B2 | 1/2011 | Tal |
| 7,879,022 B2 | 2/2011 | Bonnette |
| 7,892,273 B2 | 2/2011 | George |
| 7,896,832 B2 | 3/2011 | Zafirelis |
| 7,912,531 B1 | 3/2011 | Chiu |
| 8,034,095 B2 | 10/2011 | Randolph |
| 8,038,704 B2 | 10/2011 | Sherburne |
| 8,075,510 B2 | 12/2011 | Aklog |
| 8,167,903 B2 | 5/2012 | Hardert |
| 8,182,508 B2 | 5/2012 | Magnuson |
| 8,216,269 B2 | 7/2012 | Magnuson |
| 8,298,252 B2 | 10/2012 | Krolik |
| 8,317,859 B2 | 11/2012 | Snow |
| 8,361,095 B2 | 1/2013 | Osborne |
| 8,377,092 B2 | 2/2013 | Magnuson |
| 8,469,970 B2 | 6/2013 | Diamant |
| 8,470,016 B2 | 6/2013 | Sherburne |
| 8,475,487 B2 | 7/2013 | Bonnette |
| 8,480,702 B2 | 7/2013 | Kusleika |
| 8,613,717 B2 | 12/2013 | Aklog |
| 8,632,584 B2 | 1/2014 | Henkes |
| 8,734,374 B2 | 5/2014 | Aklog |
| 8,777,976 B2 | 7/2014 | Brady |
| 8,777,977 B2 | 7/2014 | Angel |
| 8,784,434 B2 | 7/2014 | Rosenbluth |
| 8,784,441 B2 | 7/2014 | Rosenbluth |
| 8,828,073 B2 | 9/2014 | Sherburne |
| 8,852,205 B2 | 10/2014 | Brady |
| 8,945,141 B2 | 2/2015 | Cahill |
| 8,945,170 B2 | 2/2015 | Paul, Jr. |
| 8,968,330 B2 | 3/2015 | Rosenbluth |
| 9,149,279 B2 | 10/2015 | Paul, Jr. |
| 9,149,609 B2 | 10/2015 | Ansel |
| 9,259,237 B2 | 2/2016 | Quick |
| 9,301,769 B2 | 4/2016 | Brady |
| 9,350,021 B2 | 5/2016 | Ohira |
| 9,351,749 B2 | 5/2016 | Brady |
| 9,351,861 B2 | 5/2016 | Sherburne |
| 9,393,035 B2 | 7/2016 | Yu |
| 9,402,707 B2 | 8/2016 | Brady |
| 9,408,620 B2 | 8/2016 | Rosenbluth |
| 9,439,661 B2 | 9/2016 | Johnson |
| 9,445,829 B2 | 9/2016 | Brady |
| 9,456,834 B2 | 10/2016 | Folk |
| 9,463,036 B2 | 10/2016 | Brady |
| 9,492,263 B2 | 11/2016 | Krolik |
| 9,526,864 B2 | 12/2016 | Quick |
| 9,526,865 B2 | 12/2016 | Quick |
| 9,579,116 B1 | 2/2017 | Nguyen |
| 9,642,635 B2 | 5/2017 | Vale |
| 9,642,639 B2 | 5/2017 | Brady |
| 9,700,332 B2 | 7/2017 | Marchand |
| 9,717,519 B2 | 8/2017 | Rosenbluth |
| 9,801,643 B2 | 10/2017 | Hansen |
| 9,820,769 B2 | 11/2017 | Krolik |
| 9,844,387 B2 | 12/2017 | Marchand |
| 9,855,067 B2 | 1/2018 | Krolik |
| 9,855,071 B2 | 1/2018 | Shaltis |
| 10,004,531 B2 | 6/2018 | Rosenbluth |
| 10,016,206 B1 | 7/2018 | Yang |
| 10,034,680 B2 | 7/2018 | Brady |
| 10,045,790 B2 | 8/2018 | Cox |
| 10,080,575 B2 | 9/2018 | Brady |
| 10,098,651 B2 | 10/2018 | Marchand |
| 10,201,360 B2 | 2/2019 | Vale |
| 10,238,406 B2 | 3/2019 | Cox |
| 10,265,086 B2 | 4/2019 | Vale |
| 10,278,717 B2 | 5/2019 | Brady |
| 10,285,720 B2 | 5/2019 | Gilvarry |
| 10,292,722 B2 | 5/2019 | Brady |
| 10,292,723 B2 | 5/2019 | Brady |
| 10,299,811 B2 | 5/2019 | Brady |
| 10,300,256 B2 | 5/2019 | Aboytes |
| 10,335,186 B2 | 7/2019 | Rosenbluth |
| 10,342,571 B2 | 7/2019 | Marchand |
| 10,349,960 B2 | 7/2019 | Quick |
| 10,357,265 B2 | 7/2019 | Brady |
| 10,363,054 B2 | 7/2019 | Vale |
| 10,390,850 B2 | 8/2019 | Vale |
| 10,420,570 B2 | 9/2019 | Vale |
| 10,441,301 B2 | 10/2019 | Vale |
| 10,517,622 B2 | 12/2019 | Vale |
| 10,517,708 B2 | 12/2019 | Gorochow |
| 10,524,811 B2 | 1/2020 | Marchand |
| 10,569,066 B2 | 2/2020 | Hayakawa |
| 10,582,939 B2 | 3/2020 | Brady |
| 10,588,648 B2 | 3/2020 | Brady |
| 10,588,649 B2 | 3/2020 | Brady |
| 10,588,655 B2 | 3/2020 | Rosenbluth |
| 10,610,246 B2 | 4/2020 | Brady |
| 10,617,435 B2 | 4/2020 | Vale |
| 10,667,833 B2 | 6/2020 | Vale |
| 10,675,045 B2 | 6/2020 | Brady |
| 10,682,152 B2 | 6/2020 | Vale |
| 10,729,459 B2 | 8/2020 | Krolik |
| 10,743,894 B2 | 8/2020 | Brady |
| 10,743,907 B2 | 8/2020 | Bruzzi |
| 10,772,649 B2 | 9/2020 | Hansen |
| 10,779,852 B2 | 9/2020 | Bruzzi |
| 10,792,055 B2 | 10/2020 | Brady |
| 10,792,056 B2 | 10/2020 | Vale |
| 10,799,331 B2 | 10/2020 | Hauser |
| 10,806,559 B2 | 10/2020 | Bonnette |
| 10,813,663 B2 | 10/2020 | Bruzzi |
| 10,842,498 B2 | 11/2020 | Vale |
| 10,874,421 B2 | 12/2020 | Bruzzi |
| 10,898,215 B2 | 1/2021 | Horowitz |
| 10,912,577 B2 | 2/2021 | Marchand |
| 10,952,760 B2 | 3/2021 | Brady |
| 10,953,200 B2 | 3/2021 | Sharma |
| 10,959,749 B2 | 3/2021 | Hatta |
| 11,000,682 B2 | 5/2021 | Merritt |
| 11,026,708 B2 | 6/2021 | Marks |
| 11,026,709 B2 | 6/2021 | Greenhalgh |
| 11,051,928 B2 | 7/2021 | Casey |
| 11,058,445 B2 | 7/2021 | Cox |
| 11,058,451 B2 | 7/2021 | Marchand |
| 11,076,876 B2 | 8/2021 | Vale |
| 11,154,314 B2 | 10/2021 | Quick |
| 2001/0011179 A1 | 8/2001 | Adams |
| 2001/0044598 A1 | 11/2001 | Parodi |
| 2001/0049486 A1 | 12/2001 | Evans |
| 2002/0010487 A1 | 1/2002 | Evans |
| 2002/0058964 A1 | 5/2002 | Addis |
| 2002/0072764 A1 | 6/2002 | Sepetka |
| 2002/0087119 A1 | 7/2002 | Parodi |
| 2002/0120277 A1 | 8/2002 | Hauschild |
| 2002/0143387 A1 | 10/2002 | Soetikno |
| 2002/0151918 A1 | 10/2002 | Lafontaine |
| 2002/0151922 A1 | 10/2002 | Hogendijk |
| 2002/0161377 A1 | 10/2002 | Rabkin |
| 2002/0161427 A1 | 10/2002 | Rabkin |
| 2002/0165574 A1 | 11/2002 | Ressemann |
| 2002/0173815 A1 | 11/2002 | Hogendijk |
| 2002/0188276 A1 | 12/2002 | Evans |
| 2003/0023204 A1 | 1/2003 | Vo |
| 2003/0055445 A1 | 3/2003 | Evans |
| 2003/0093112 A1 | 5/2003 | Addis |
| 2003/0149467 A1 | 8/2003 | Linder |
| 2003/0195537 A1 | 10/2003 | Dubrul |

(56) References Cited

U.S. PATENT DOCUMENTS

| | | |
|---|---|---|
| 2003/0199890 A1 | 10/2003 | Dubrul |
| 2003/0236533 A1 | 12/2003 | Wilson |
| 2004/0019310 A1* | 1/2004 | Hogendijk ............ A61B 17/22 604/1 |
| 2004/0064179 A1 | 4/2004 | Linder |
| 2004/0082962 A1 | 4/2004 | Demarais |
| 2004/0147939 A1 | 7/2004 | Rabkin |
| 2004/0176659 A1 | 9/2004 | Peng |
| 2004/0181237 A1 | 9/2004 | Forde |
| 2004/0210298 A1 | 10/2004 | Rabkin |
| 2004/0260333 A1 | 12/2004 | Dubrul |
| 2005/0004594 A1 | 1/2005 | Nool |
| 2005/0080431 A1 | 4/2005 | Levine |
| 2005/0080480 A1 | 4/2005 | Bolea |
| 2005/0177022 A1 | 8/2005 | Chu |
| 2006/0009785 A1 | 1/2006 | Maitland |
| 2006/0041228 A1 | 2/2006 | Vo |
| 2006/0041304 A1 | 2/2006 | Jang |
| 2006/0047266 A1 | 3/2006 | Elkins |
| 2006/0047300 A1 | 3/2006 | Eidenschink |
| 2006/0095015 A1 | 5/2006 | Hobbs |
| 2006/0129095 A1 | 6/2006 | Pinchuk |
| 2006/0189930 A1 | 8/2006 | Lary |
| 2006/0195138 A1 | 8/2006 | Goll |
| 2006/0200191 A1 | 9/2006 | Zadno-Azizi |
| 2006/0253145 A1 | 11/2006 | Lucas |
| 2007/0027520 A1 | 2/2007 | Sherburne |
| 2007/0038241 A1 | 2/2007 | Pal |
| 2007/0118072 A1 | 5/2007 | Nash |
| 2007/0238917 A1 | 10/2007 | Peng |
| 2007/0239182 A1 | 10/2007 | Glines |
| 2008/0033482 A1 | 2/2008 | Kusleika |
| 2008/0041516 A1 | 2/2008 | Chiu |
| 2008/0065008 A1 | 3/2008 | Barbut |
| 2008/0103439 A1 | 5/2008 | Torrance |
| 2008/0249558 A1 | 10/2008 | Cahill |
| 2009/0018567 A1 | 1/2009 | Escudero |
| 2009/0054918 A1 | 2/2009 | Henson |
| 2009/0099581 A1 | 4/2009 | Kim |
| 2009/0137984 A1 | 5/2009 | Minnelli |
| 2009/0163846 A1 | 6/2009 | Aklog |
| 2009/0222035 A1 | 9/2009 | Schneiderman |
| 2009/0292307 A1 | 11/2009 | Razack |
| 2009/0306702 A1 | 12/2009 | Miloslavski |
| 2010/0030327 A1 | 2/2010 | Chatel |
| 2010/0057184 A1 | 3/2010 | Randolph |
| 2010/0274277 A1 | 10/2010 | Eaton |
| 2011/0190806 A1 | 8/2011 | Wittens |
| 2011/0213290 A1 | 9/2011 | Chin |
| 2011/0213392 A1 | 9/2011 | Aklog |
| 2012/0016455 A1 | 1/2012 | Sherburne |
| 2012/0059309 A1 | 3/2012 | Di Palma |
| 2012/0059356 A1 | 3/2012 | Di Palma |
| 2012/0150193 A1 | 6/2012 | Aklog |
| 2012/0197277 A1 | 8/2012 | Stinis |
| 2012/0253358 A1 | 10/2012 | Golan |
| 2013/0090624 A1 | 4/2013 | Munsinger |
| 2013/0289694 A1 | 10/2013 | Sherburne |
| 2013/0304082 A1 | 11/2013 | Aklog |
| 2014/0155908 A1 | 6/2014 | Rosenbluth |
| 2014/0171958 A1 | 6/2014 | Baig |
| 2014/0296868 A1* | 10/2014 | Garrison ............... A61B 17/22 606/127 |
| 2014/0324091 A1 | 10/2014 | Rosenbluth |
| 2014/0350591 A1 | 11/2014 | Sherburne |
| 2015/0018859 A1 | 1/2015 | Quick |
| 2015/0127044 A1 | 5/2015 | Cahill |
| 2015/0238207 A1 | 8/2015 | Cox |
| 2015/0305756 A1 | 10/2015 | Rosenbluth |
| 2015/0352325 A1 | 12/2015 | Quick |
| 2015/0360001 A1 | 12/2015 | Quick |
| 2016/0008014 A1 | 1/2016 | Rosenbluth |
| 2016/0038174 A1 | 2/2016 | Bruzzi |
| 2016/0095744 A1 | 4/2016 | Wolfertz |
| 2016/0143721 A1 | 5/2016 | Rosenbluth |
| 2016/0206344 A1 | 7/2016 | Bruzzi |
| 2016/0262790 A1 | 9/2016 | Rosenbluth |
| 2016/0287276 A1 | 10/2016 | Cox |
| 2017/0079672 A1 | 3/2017 | Quick |
| 2017/0105745 A1 | 4/2017 | Rosenbluth |
| 2017/0112513 A1 | 4/2017 | Marchand |
| 2017/0112514 A1 | 4/2017 | Marchand |
| 2017/0189041 A1 | 7/2017 | Cox |
| 2017/0265878 A1 | 9/2017 | Marchand |
| 2017/0325839 A1 | 11/2017 | Rosenbluth |
| 2017/0333076 A1 | 11/2017 | Bruzzi |
| 2018/0092652 A1 | 4/2018 | Marchand |
| 2018/0193043 A1 | 7/2018 | Marchand |
| 2018/0256178 A1 | 9/2018 | Cox |
| 2018/0271556 A1 | 9/2018 | Bruzzi |
| 2018/0296240 A1 | 10/2018 | Rosenbluth |
| 2018/0344339 A1 | 12/2018 | Cox |
| 2018/0361116 A1 | 12/2018 | Quick |
| 2019/0046219 A1 | 2/2019 | Marchand |
| 2019/0070401 A1 | 3/2019 | Merritt |
| 2019/0150959 A1 | 5/2019 | Cox |
| 2019/0231373 A1 | 8/2019 | Quick |
| 2019/0321071 A1 | 10/2019 | Marchand |
| 2020/0046368 A1 | 2/2020 | Merritt |
| 2020/0178991 A1 | 6/2020 | Greenhalgh |
| 2021/0022766 A1 | 1/2021 | Bruzzi |
| 2021/0113224 A1 | 4/2021 | Dinh |
| 2022/0104839 A1 | 4/2022 | Horowitz |
| 2022/0104840 A1 | 4/2022 | Horowitz |
| 2022/0125456 A1 | 4/2022 | Horowitz |
| 2022/0240959 A1 | 8/2022 | Quick |
| 2022/0346813 A1 | 11/2022 | Quick |
| 2022/0346814 A1 | 11/2022 | Quick |
| 2023/0046775 A1 | 2/2023 | Quick |

FOREIGN PATENT DOCUMENTS

| | | |
|---|---|---|
| AU | 2018328011 | 3/2020 |
| CA | 2939315 | 12/2015 |
| CA | 3002154 | 4/2017 |
| CA | 3074564 | 3/2019 |
| CN | 1278713 | 1/2001 |
| CN | 1486758 | 4/2004 |
| CN | 108472052 | 8/2018 |
| CN | 109069790 | 12/2018 |
| CN | 110312481 | 10/2019 |
| EP | 2897536 | 7/2015 |
| EP | 3094363 | 11/2016 |
| EP | 3364891 | 8/2018 |
| EP | 3389757 | 10/2018 |
| EP | 3528717 | 8/2019 |
| JP | H025976 | 1/1990 |
| JP | 2003521286 | 7/2003 |
| JP | 2006015058 | 1/2006 |
| JP | 2007319272 | 12/2007 |
| JP | 6438495 | 12/2018 |
| JP | 2018537229 | 12/2018 |
| JP | 2018538027 | 12/2018 |
| WO | 9945835 | 9/1999 |
| WO | 2005079678 A1 | 9/2005 |
| WO | 2006063199 | 6/2006 |
| WO | 2010119110 | 10/2010 |
| WO | 2011144336 | 11/2011 |
| WO | 2012156924 | 11/2012 |
| WO | 2014141226 | 9/2014 |
| WO | 2016071524 | 5/2016 |
| WO | 2017070702 | 4/2017 |
| WO | 2017106877 | 6/2017 |
| WO | 2019050765 | 3/2019 |
| WO | 2021076954 | 4/2021 |
| WO | 2022082213 | 4/2022 |

OTHER PUBLICATIONS

Greenfield et al., Transvenous Removal of Pulmonary Emboli by Vacuum-Cup Catheter Technique, Journal of Surgical Research, vol. 9, No. 6 (Jun. 1969) pp. 347-352.

(56) References Cited

OTHER PUBLICATIONS

PCT International Search Report based on PCT/US2008/072352 dated Nov. 4, 2008, 1 page.
U.S. Appl. No. 17/190,268, Jul. 17, 2018, Zhao.
International Search Report and Written Opinion for PCT/US2012/032291 dated Aug. 10, 2012, 14 pages.
International Search Report and Written Opinion for PCT/US2012/032295 dated Jul. 6, 2012, 13 pages.
International Search Report and Written Opinion for PCT/US2012/032306 dated Aug. 13, 2012, 12 pages.
International Search Report and Written Opinion for PCT/US2012/032311 dated Sep. 7, 2012, 14 pages.
International Search Report EP03252158_AESR dated Aug. 29, 2003, 1 page.
International Search Report EP08864356_SESR dated Apr. 1, 2014, 2 pages.
International Search Report PCT-NL-08-050399 ISR dated Feb. 13, 2009, 3 pages.
International Search Report PCT-US-08-072352 IPRP dated Nov. 4, 2008, 11 pages.
International Search Report PCT-US-12-032291 IPRP dated Aug. 10, 2012, 11 pages.
International Search Report PCT-US-12-032299 IPRP dated Oct. 2, 2012, 7 pages.
International Search Report PCT-US-12-032299 ISR dated Oct. 2, 2012, 3 pages.
International Search Report PCT-US-12-032299_WOSA dated Oct. 2, 2012, 6 pages.
International Search Report PCT-US-12-032306 IPRP dated Aug. 13, 2012, 6 pages.
International Search Report PCT-US-12-032306 ISR dated Aug. 13, 2012, 2 pages.
International Search Report PCT-US-12-032306_WOSA dated Aug. 13, 2012, 5 pages.
International Search Report PCT-US-12-032311 IPRP dated Sep. 7, 2012, 6 pages.
International Search Report PCT-US-12-032311_ISR dated Sep. 7, 2012, 4 pages.
International Search Report PCT-US-12-032311_WOSA dated Sep. 7, 2012, 5 pages.
Nael et al., Endovascular Management of Central Thoracic Veno-Occlusive Diseases in Hemodialysis Patients: a Single Institutional Experience in 69 Consecutive Patients, Journal of Vascular Interventional Radiology, vol. 20, No. 1, 2009, pp. 46-51.
Non-Final Office Action in U.S. Appl. No. 12/187,121, dated Mar. 22, 2011, 14 pages.
Notice of Allowance dated Jan. 25, 2023 for U.S. Appl. No. 16/458,529 (pp. 1-2).
Notice of Allowance dated Nov. 1, 2022 for U.S. Appl. No. 16/458,529 (pp. 1-5).
Notice of Allowance dated May 12, 2022 for U.S. Appl. No. 16/797,188 (pp. 1-11).
Office Action cited in U.S. Appl. No. 12/187,121 dated May 18, 2011, 14 pages.
Office Action dated Jan. 19, 2023 for U.S. Appl. No. 16/279,216 (pp. 1-66).
Office Action dated Sep. 23, 2022 for U.S. Appl. No. 16/279,216 (pp. 1-10).
Office Action dated Apr. 8, 2022 for U.S. Appl. No. 16/279,216 (pp. 1-14).
Office Action dated Dec. 17, 2021 for U.S. Appl. No. 16/279,216 (pp. 1-11).
Office Action dated Dec. 30, 2020 for U.S. Appl. No. 16/279,216 (pp. 1-10).
Office Action dated Jul. 5, 2022 for U.S. Appl. No. 16/458,529 (pp. 1-8).
Office Action dated Jul. 12, 2021 for U.S. Appl. No. 16/279,216 (pp. 1-12).
Office Action dated Mar. 8, 2021 for U.S. Appl. No. 16/454,644 (pp. 1-9).
Valji, et al, Pulsed-Spray Thrombolysis of Arterial and Bypass Graft Occlusion, American Roentgen Ray Society, pp. 617-621 (Mar. 1991).

* cited by examiner

DEVICE AND METHOD FOR MANUAL ASPIRATION AND REMOVAL OF AN UNDESIRABLE MATERIAL

CROSS-REFERENCE TO RELATED APPLICATIONS

This application claims priority to U.S. provisional application No. 62/971,280, filed on Feb. 7, 2020, of which are incorporated herein by reference in their entirety.

TECHNICAL FIELD

This disclosure relates generally to devices, systems, and methods for removing undesirable material from a site of interest within the circulatory system. Included herein are systems and methods for manually generating a suction force or vacuum force for removing substantially en bloc any undesired material (natural and/or unnatural) including, but not limited to, clots, thrombus, embolus, vegetational growths, infected tissue, or other undesirable intravascular material ("UIM") from within heart chambers, blood vessels, or any other treatment site during a minimally invasive percutaneous procedure. The aspirated bodily fluid and undesirable material may be collected in a waste assembly for disposal, or alternatively the aspirated undesirable material may be filtered (to be removed) and the aspirated bodily fluid to be reinfused back into the patient's body.

BACKGROUND OF THE INVENTION

Many patients suffer from the presence of undesirable material, most notably blood clots, in the circulatory system including, but not limited to, blood vessels and heart chambers. Examples of such diseases include, but are not limited to, myocardial infarction, stroke, pulmonary embolism, deep venous thrombosis, atrial fibrillation, infective endocarditis, etc.

The circulatory system can be disrupted by the presence of undesirable material, most commonly blood clots, but also tumor, infective vegetations, and foreign bodies, etc. Blood clots can arise spontaneously within the blood vessel or heart chamber (thrombosis) or be carried through the circulation from a remote site and lodge in a blood vessel (thromboemboli).

There are many existing techniques to remove undesirable material from the circulatory system; for example, the delivery of pharmaceutical agents (such as thrombolytic agents); mechanical treatments (such as aspiration and/or mechanical maceration); catheter-based removal techniques (such as catheter pulmonary embolectomy); or other general surgical treatments.

There is a need in the art for an improved systems and methods to endovascularly remove undesirable material from a patient's body.

SUMMARY

In one embodiment, the device comprises a handle body, a trigger assembly, a plunger assembly, a plunger rod, a barrel, and a connection assembly. The trigger assembly is connected to a distal end of the plunger rod; a distal end of the handle body is connected to a proximal end of the barrel. The connection assembly comprises a barrel inlet channel, a waste port channel, an inlet valve, outlet valve, an inlet connector to be operatively coupled to a suction cannula, and an outlet connector to be operatively coupled to a waste assembly, the connection assembly is connected to a distal end of the barrel; and wherein at least a section of the plunger rod and the plunger assembly are co-axially positioned within the barrel.

The suction cannula lumen, the barrel inlet channel, the inlet valve, a cavity of the barrel, the waste port channel, and the waste assembly are all in fluid communication.

The handle body comprises an upper slot, a volume limiter assembly, a vacuum locking mechanism, and a lower slot.

The trigger assembly further comprises an upper tab and a lower tab; and wherein the upper tab is configured to slideably move within upper slot and the lower tab is configured to slideably move within the lower slot.

The volume limiter assembly comprises a first volume setting and a second volume setting; wherein the first volume setting is less than the second volume setting; and wherein the volume limiter assembly is configured to engage with the upper tab.

The inlet valve further comprises an inlet one-way valve, and the outlet valve comprises an outlet one-way valve; and wherein the inlet one-way valve is orientated in an opposite direction as the outlet one-way valve.

The vacuum locking mechanism is configured to engage with the upper tab to lock the trigger assembly in an aspiration position.

The movement of the trigger in a first direction is configured to generate a suction force through the barrel inlet channel, the inlet valve, and a cavity of the barrel; and wherein movement of the trigger in a second direction is configured to generate a drive force through the waste port channel, the outlet valve, and the cavity of the barrel.

The vacuum locking mechanism comprises an engaged position and a disengaged position; wherein when the vacuum locking mechanism is in the engaged position the vacuum locking mechanism is configured to limit the movement of the trigger assembly such that the device continuously generates the suction force.

Both the inlet one-way valve and outlet one-way valve are configured to allow the undesirable material to pass through substantially en bloc.

In another embodiment, the system includes an aspiration device comprising a handle body, a trigger assembly, a pump assembly, and a connection assembly; the trigger assembly and the handle body are both connected to a distal end of the pump assembly, the connection assembly is connected to a proximal end of the pump assembly; the connection assembly comprises a barrel inlet channel, a waste port channel, an inlet valve, an outlet valve, an inlet connector to be operatively coupled to a suction cannula, and an outlet connector to be operatively coupled to a waste assembly. The suction cannula comprising an expandable funnel at a suction cannula distal end. The waste assembly comprising a waste tube and a waste bag. The expandable funnel, the inlet valve, and the outlet valve are configured such that the undesirable material flows through the expandable funnel, the inlet valve, and the outlet valve substantially en bloc.

The aspiration device further comprises a volume limiter assembly and a vacuum lock assembly.

The volume limiter assembly further comprises a first volume setting and a second volume setting; and wherein the vacuum lock assembly further comprises a vacuum lock position and a vacuum unlocked position. The first volume setting is 10 cc and the second volume setting is 30 cc.

The system may further comprise a secondary device configured to aid in the en bloc removal of the undesirable material.

In another embodiment, the method for removing an undesirable material from a patient comprises placing a suction cannula within a vessel of the patient, the suction cannula comprising a suction cannula lumen, a suction cannula distal end, and a suction cannula proximal end. Connecting the suction cannula proximal end to a suction cannula port of an aspiration device, the aspiration device comprising a handle, a trigger, a pump assembly, the suction cannula port, and a waste assembly port; wherein the pump assembly is configured to generate both a vacuum force and a drive force. Connecting a waste assembly to the waste assembly port. Navigating the suction cannula to a treatment site within the vessel. Activating the trigger such that the pump assembly generates the vacuum force through the suction cannula lumen and the suction cannula distal end, thereby aspirating the undesirable material from the vessel substantially en block. Releasing the trigger such that the pump assembly generates the drive force through the waste assembly port and removes the aspirated undesirable material from the pump assembly and into the waste assembly.

The method may further comprise the step of priming the aspiration device, the step of priming the aspiration device comprising the steps of opening an accessory port of the aspiration device to provide for blood bleed back; closing the accessory port; setting a volume limiter of aspiration device to a first volume setting; tilting the handle; and pulling the trigger.

The method further comprises a step of activating the trigger further comprises either: (i) manually pumping the trigger such that the pump assembly alternately generates the vacuum force and the drive force; or (ii) activate a vacuum lock mechanism of the aspiration device such that the pump assembly continuously generates the suction force.

The method further comprises a step of activating the trigger such that the pump assembly generates the suction force through the suction cannula lumen and the suction cannula distal end further comprises the user receiving a tactile feedback response from the trigger. The tactile feedback response comprises an increase in a resistance the user feels when activating the trigger.

The method may further comprise the step of monitoring the waste assembly to determine if the waste assembly is full or needs to be replaced.

BRIEF DESCRIPTION OF THE DRAWINGS

The foregoing purposes and features, as well as other purposes and features, will become apparent with reference to the description and accompanying figures below, which are included to provide an understanding of the invention and constitute a part of the specification, in which like numerals represent like elements, and in which:

FIG. 6A shows the device in a resting position. FIG. 6B shows the device in a partially retracted position. FIG. 6C shows the device in a fully retracted position.

FIG. 12A illustrates the assembly in a locked position. FIG. 12B shows the assembly in an unlocked position.

DETAILED DESCRIPTION OF THE INVENTION

Figure 1:
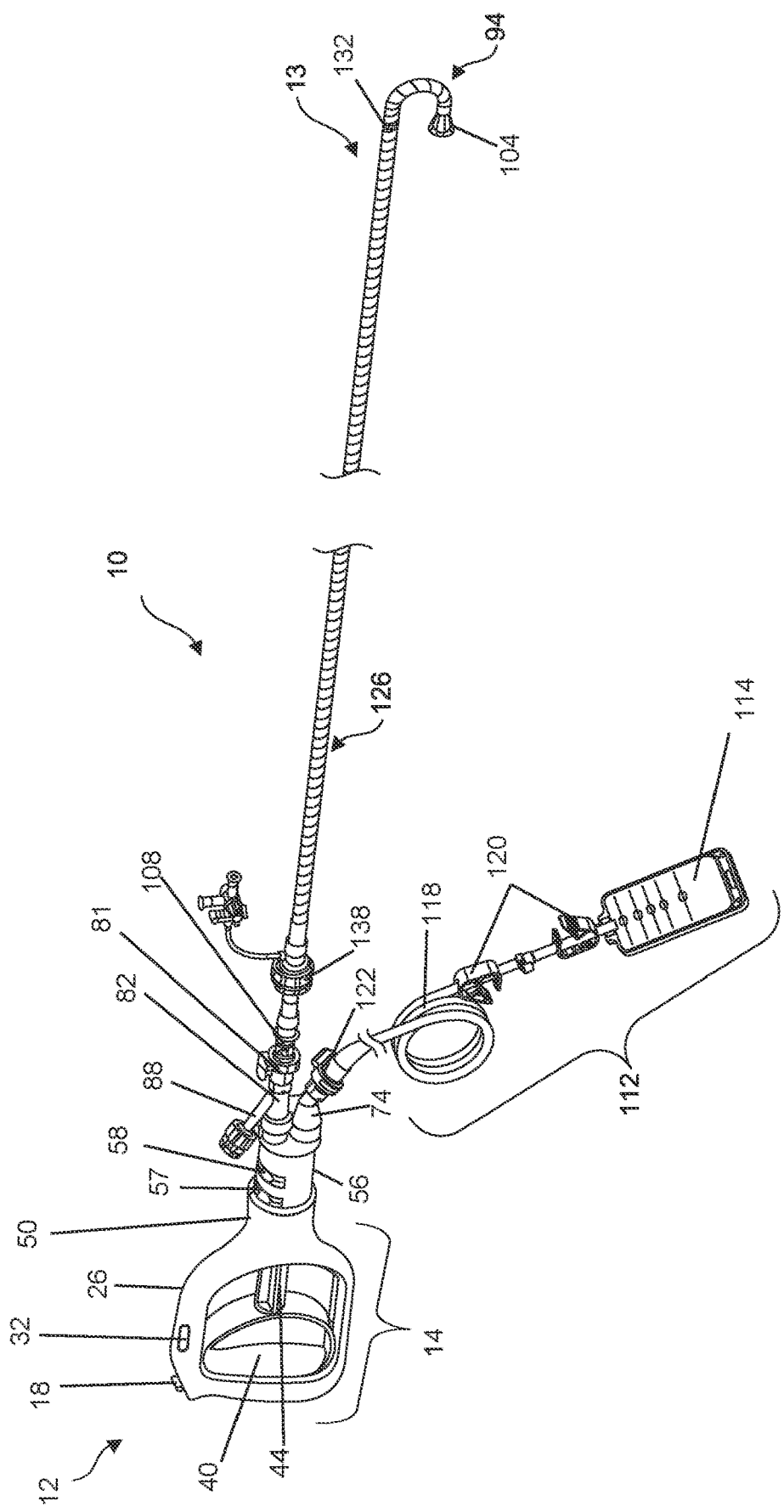
FIG. 1 illustrates a view of an assembled aspiration system in accordance with some embodiments.
Figure 2:
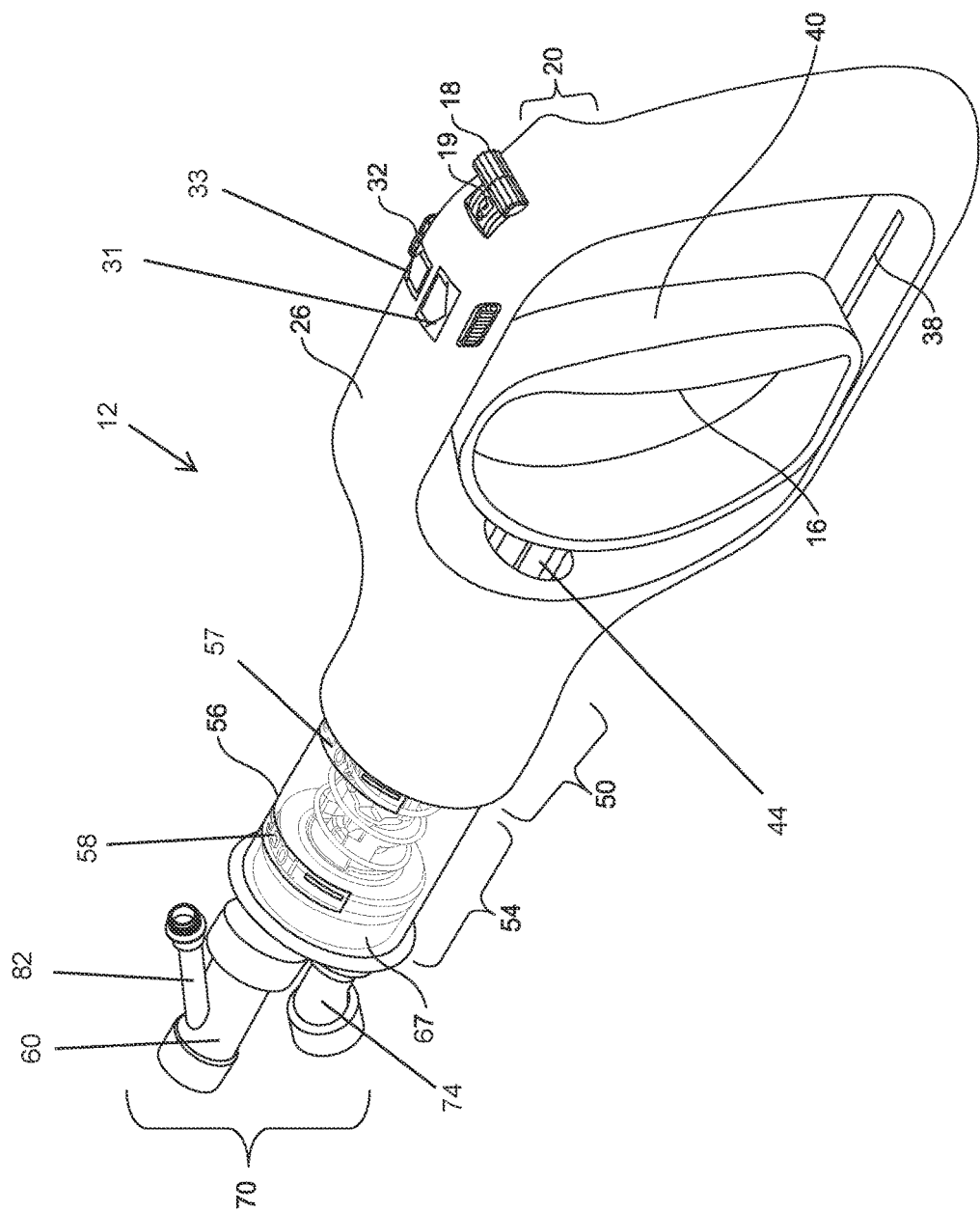
FIG. 2 illustrates a view of an aspiration device shown in a resting position.
Figure 3:
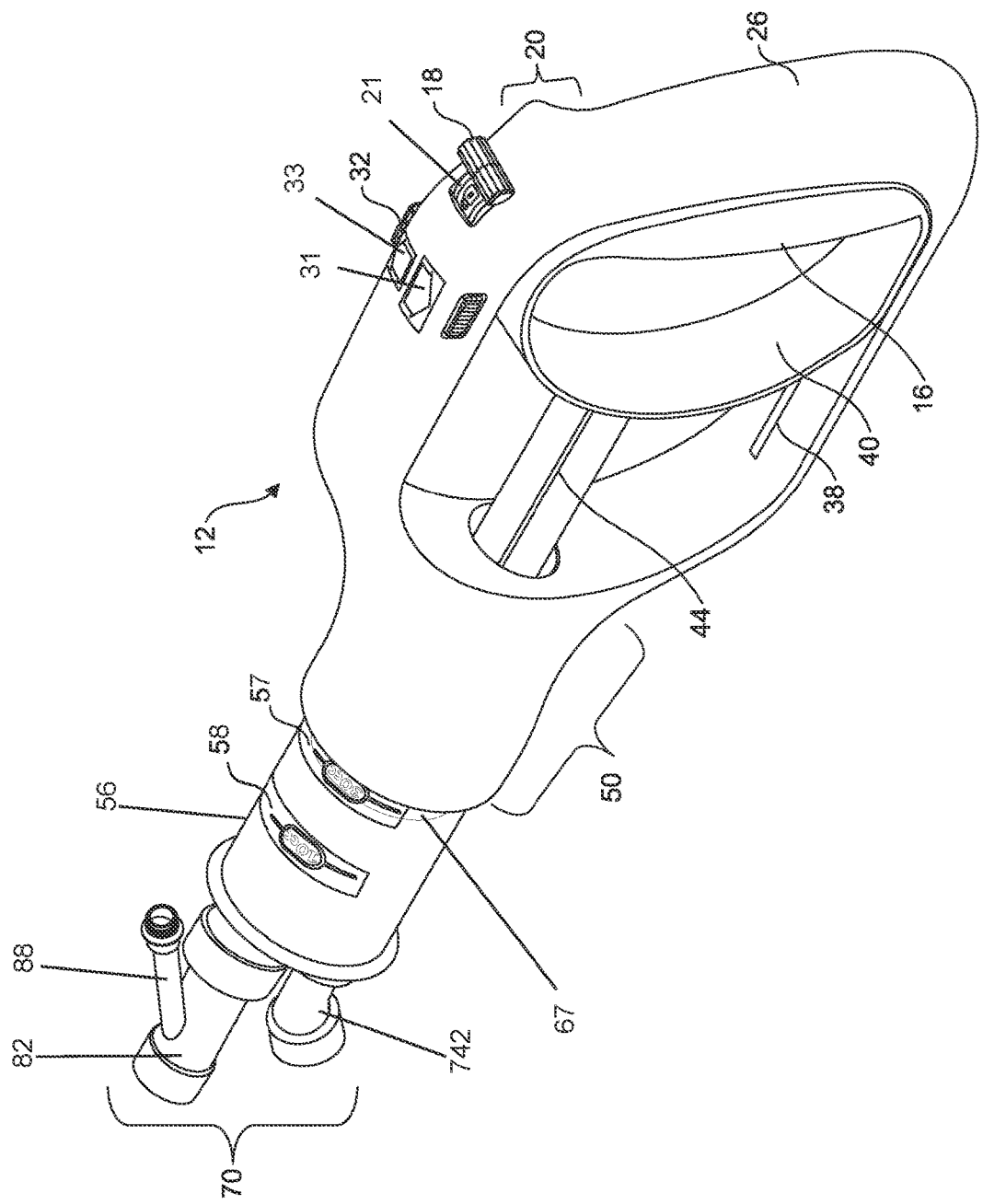
FIG. 3 illustrates a view of the aspiration device of FIG. 2 shown a fully retracted position.

The drawings, which are not necessarily to scale, depict selected embodiments and are not intended to limit the scope of the disclosure. The detailed description illustrates by way of example, not by way of limitation, selected embodiments.

The skilled artisan will readily appreciate that the devices and methods described herein are merely exemplary and that variations can be made without departing from the spirit and scope of the invention. It is also to be understood that the terminology used herein is for the purpose of describing particular embodiments only and is not intended to be limiting.

Referring now in detail to the drawings, in which like reference numerals indicate like parts or elements throughout the several views, in various embodiments, presented herein the devices and methods for minimally invasive removal of undesirable material (UIM) from a vessel or other hollow anatomical structure of a patient.

Proximal and distal refer to a direction or location relative to the patient's center. A proximal direction is course of movement away from the patient's center and toward the user. A proximal location is a position which further away from the patient's center and closer to the operator. A distal direction is a course movement toward the patient's center and away from the user. A proximal location refers to location further from the patient's center than a second location of the device during use. A distal location refers to a location nearer to the patient's center compared with a second location of the device during use.

Undesirable intravascular material (UIM) refers to intravascular debris including, but not limited to, thrombus; embolus; clot; vegetative growth; infected vegetative growth (such as endocarditis); pulmonary embolism; tumor; arterial clots, undesirable material trapped in dialysis grafts and/or stents, and other undesirable natural and/or unnatural foreign bodies to be removed from a patient's body.

Target vessels, treatment sites, or target areas include, but are not limited to, systemic venous circulation (e.g., inferior vena cava and/or superior vena cava, pelvic veins, leg veins, neck and arm veins); arterial circulation (e.g., aorta or its large and medium branches); heart chambers (for example, in the left heart (e.g., the left ventricular apex and left atrial appendage), right heart (e.g., right atrium and right ventricle), or on its valves); small blood vessels; medium blood vessels, large blood vessels; iliofemoral vein; peripheral vasculature; and/or the pulmonary circulation (e.g., pulmonary veins and/or pulmonary arteries); Also included are other nonvascular tubular structures including, but not limited to, ducts, or any other avascular tubular tissue. Other treatment sites or target areas include, but not limited to pacemaker leads, stents, or other artificial implanted medical devices.

En bloc refers to entirely, wholly, and/or without significant fragmentation.

A suction force and/or vacuum force refers to the negative pressure created by removing air from a space creating a pressure differential resulting in the force that a vacuum exerts upon the UIM. A drive force refers to the pressure differential generated by the device that exerts a force upon the UIM.

Differential pressure is the difference in pressure between two given points. Positive pressure refers to the pressure at a first point that is greater than pressure at a second point. Negative pressure refers a pressure at a first point that is lower than pressure at a second point.

A vacuum is defined herein refers to a differential pressure, including decreases in pressure (negative pressure) below atmospheric pressure and increases in pressure (positive pressure) above atmospheric bidirectional differential pressure. For example, a vacuum or negative pressure for the suction force ranges from −11 psi to −14.7 psi, and a positive pressure for the driving force ranges from +1 psi to +10 psi (i.e., the range of the return spring force).

A trigger pull cycle is defined as the combined retraction or compression and release of the trigger assembly. Fully retracted is defined as a maximum distance of travel for the trigger assembly starting from a rest position and/or deactivated state. Partially retracted is defined as any distance between the trigger assembly at a rest position and/or deactivated state and a full retraction of the trigger assembly, i.e., some distance less than the possible maximum distance of travel for the trigger assembly starting from a rest position and/or deactivated state.

The term below defined herein refers to any point along a plane below

This disclosure relates to devices and methods for minimally invasive removal of undesirable material (UIM) from a vessel or other hollow anatomical structure of a patient. More specifically, in one embodiment this disclosure relates to a mechanical aspiration system which facilitates en bloc removal of the UIM using a disposable, manually operated aspiration device coupled to, and in fluid communication with, a suction cannula and waste assembly. The suction cannula comprises an expandable funnel distal end to aid in the en bloc removal of the UIM. The manually operated aspiration device provides for single-handed operation and manual control of generating a suction force and/or a drive force during the removal of UIM from the patient.

Referring to FIGS. 1-15, aspiration system 10 comprises a suction cannula/procedure sheath subassembly 13, a manually operated aspiration device 12, and a waste collection assembly 112. The aspiration device 12 comprises a handle body 26, a trigger assembly 40, a pump assembly 54, and a connector body 70. The suction cannula/procedural sheath subassembly 13 comprises a suction cannula 94 and a procedural sheath 126. The waste collection assembly 112 comprises a waste collection assembly tubing 118, pinch valves 120, and a waste collection receptacle 114.

The handle subassembly 14 comprises a grip portion 16, vacuum lock actuator 18, a hilt portion 20, a handle body 26, an upper handle slot 30, a lower handle slot 38, a volume limiter, and a vacuum locking mechanism 34. The volume limiter comprises a volume limiter actuator element 32 and a travel stop.

Handle subassembly 14 provides single-handed operator control of fluid aspiration and negative pressure during a clot removal procedure. The handle subassembly 14 is comprised of a handle body 26, trigger assembly 40 and distal handle section 50. Handle body 26 comprises a handle base, an outer gripping surface, an inner gripping surface, handle body upper section 28, handle body lower section 36, and handle distal section 50.

Figure 6A:
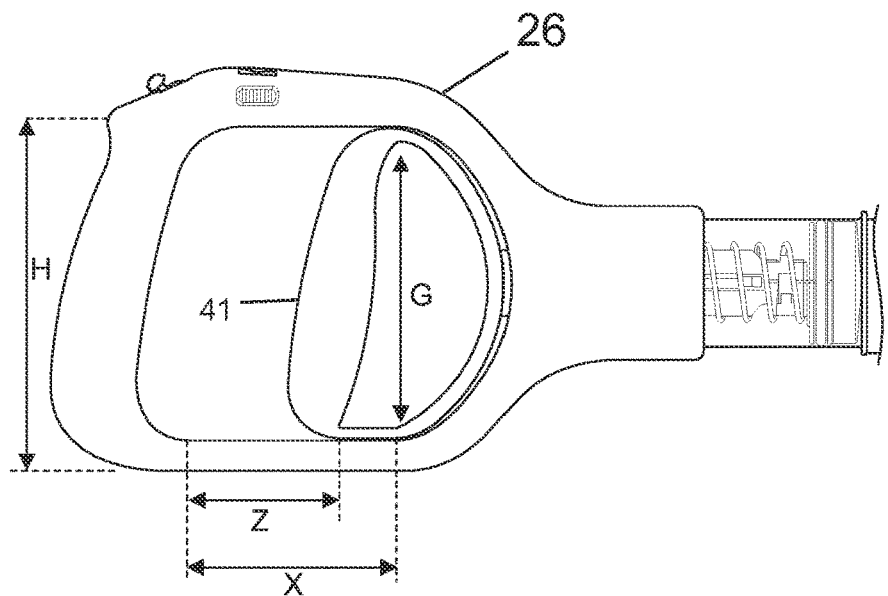
FIG. 6A-FIG. 6C illustrate partial side views of an aspiration device in accordance with some embodiments.
Figure 6B:
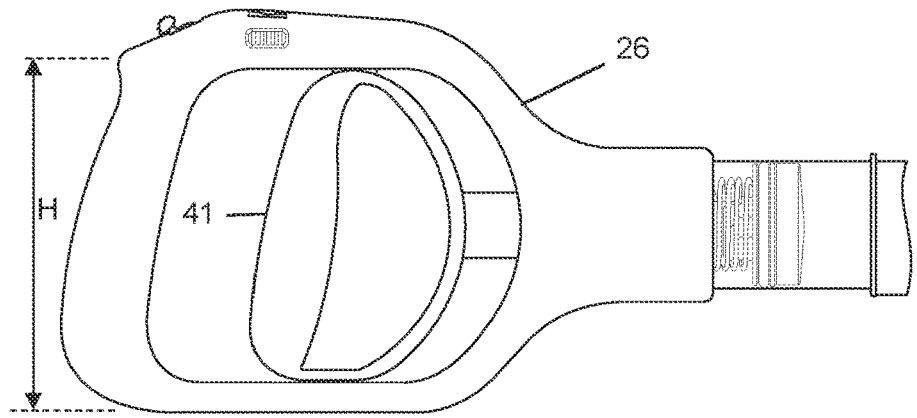
Figure 6C:
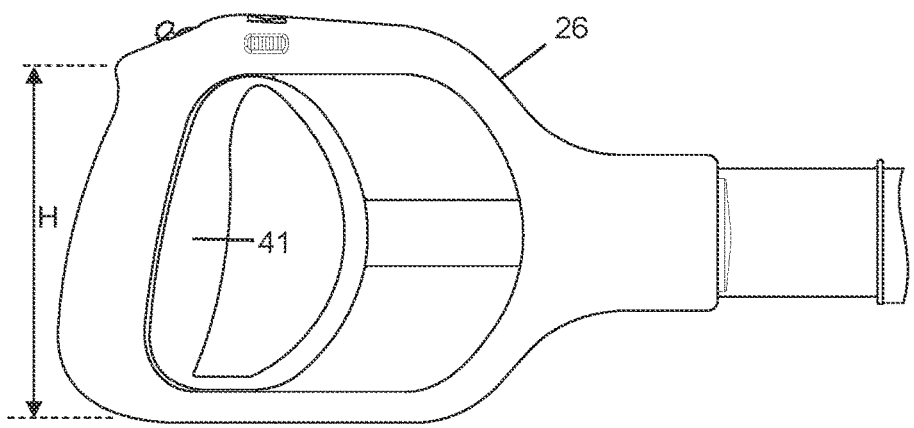

The trigger assembly 40 comprises a resting position (as shown in FIG. 6A) and a first activated position (shown in FIG. 6B) and a fully activated position (shown in FIG. 6C). When the trigger assembly 40 is in the resting position no aspiration or suction force is generated by the pump assembly 54. When the trigger assembly 40 is moved by the user to the active position the aspiration device 12 is configured to generate an aspiration force or a suction force (as described in more detail below). As the user releases their grip on the trigger assembly 40, the trigger assembly 40 is configured to move (as a result of the spring force generated by spring 64) from the activated position to toward the resting position, and the device 12 is configured to generate a drive force (as described in more detail below).

Figure 7:
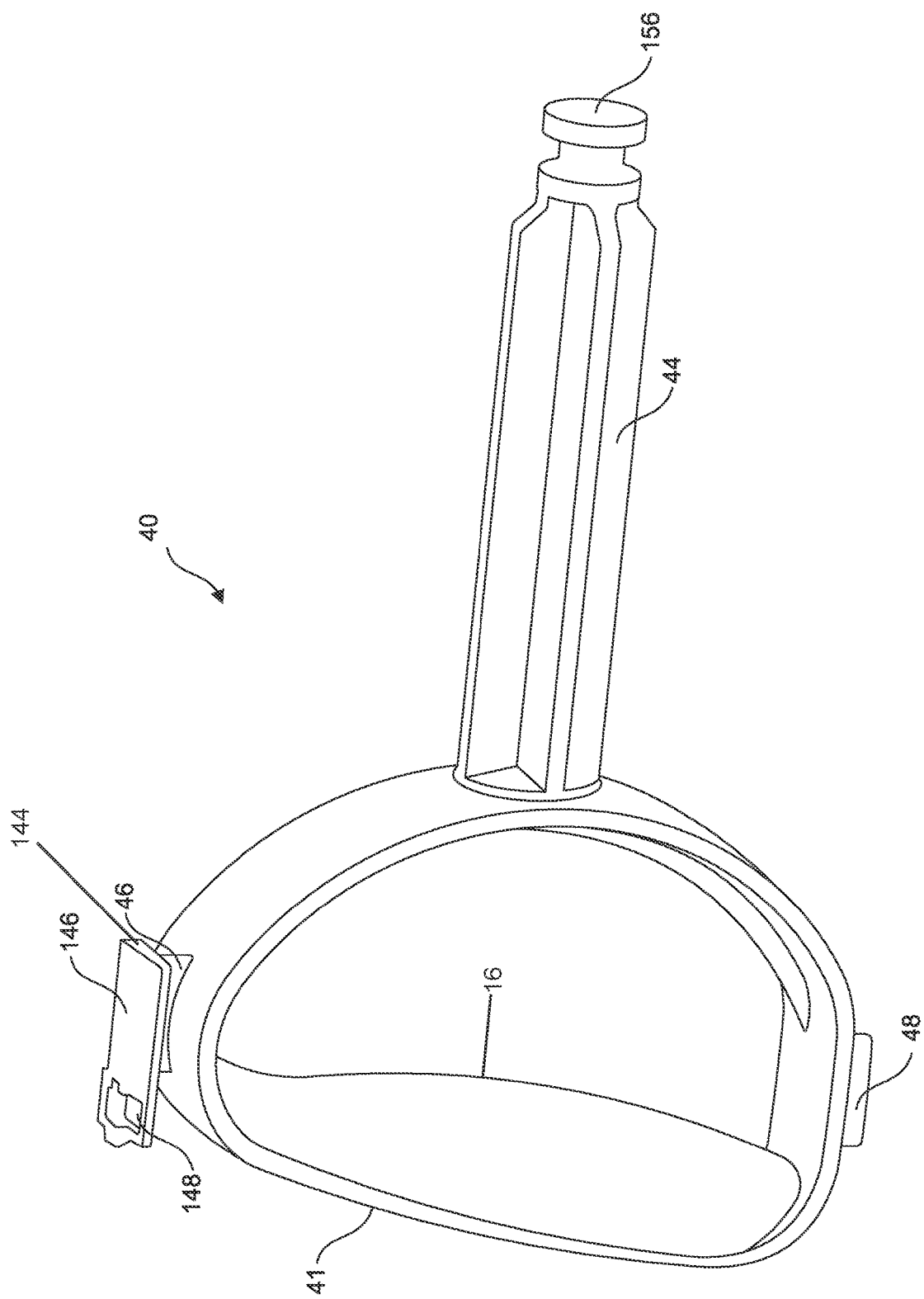
FIG. 7 illustrates a view of a trigger subassembly in accordance with some embodiments.
Figure 8:
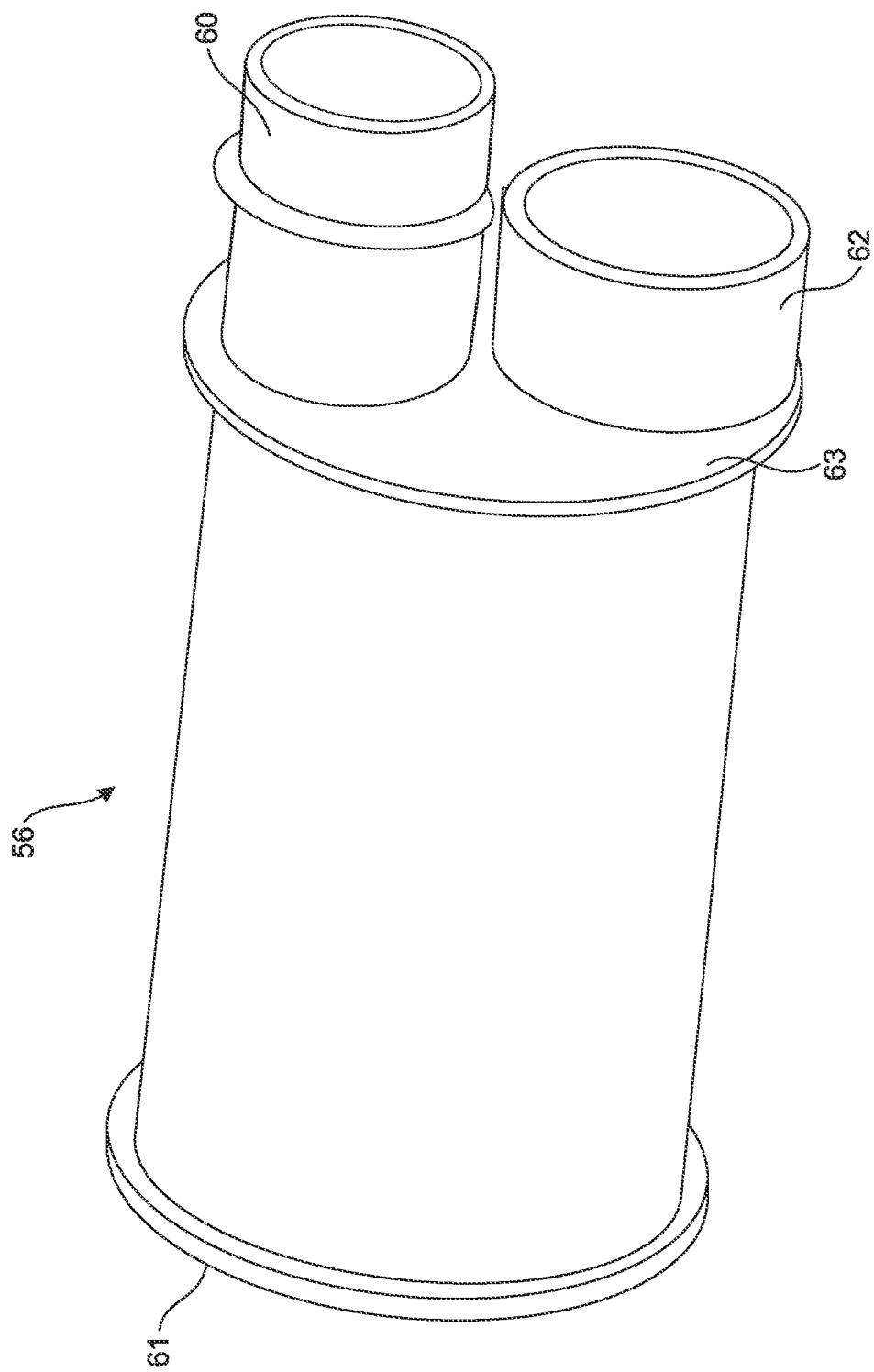
FIG. 8 illustrates a view of a barrel in accordance with some embodiments.

To activate the aspiration, generate vacuum, and/or generate an aspiration force, the user grips the trigger assembly 40, and with their palm resting against the grip portion 16 of handle body 26, pulls the trigger assembly 40 proximally. Handle body 26 and trigger assembly 40 are dimensioned and contoured to facilitate ease of use, optimize user grip and stability during use, and reduce a potential of user hand fatigue during repeated pull cycles. For example, hilt portion 20 of handle body 26 may prevent a user's hand from slipping while gripping or holding the handle body 2; create a contour to securely keep the user's hand in place during use; and/or dimensioned to allow the user to reach the top of device with a finger during use. In one embodiment, handle subassembly 14 is sized to accommodate differences in user hand preferences (left or right hand), hand strengths, and hand sizes. The total length grip portion 16 of handle body 26 (shown as "H" in FIGS. 6A-6C) may have an overall height of approximately 2.5-3.5 inches to accommodate the span of most palm sizes. The maximum trigger span (as shown by "Z" in FIG. 6A) is defined as maximum distance between the trigger assembly 40 at a full rest position (as shown in FIG. 6A) and when trigger assembly 40 is at a maximum activation position (as shown in FIG. 6C). The maximum trigger span is configured to ensure that users, regardless of hand size, can both grasp the trigger assembly 40 and operate the aspiration device 12 within an optimal force range (i.e., move the trigger assembly to any position between the full rest position and the maximum activation position). The maximum trigger span (as shown by "Z" in FIG. 6A) is the total distance in which the lower tab 48 (as shown in FIG. 7) can slideably travel within the lower handle slot 38. In one embodiment, the maximum trigger assembly 40 travel is between 1.2 and 1.7 inches to accommodate the majority of operator hand sizes. The maximum span of the lower handle slot (as shown by "X" in FIG. 6A) is a select distance longer than the maximum trigger span (as shown by "Z" in FIG. 6A).

In one embodiment the handle subassembly 14 is designed as a single use assembly, thereby avoiding the need to re-sterilize the device after each use. However, in another embodiment the handle subassembly 14 may be multi-use and could be re-sterilized or re-purposed between uses if needed.

Trigger assembly 40 (as shown from an isometric view in FIG. 7) provides for single-handed control over aspiration of fluids and undesirable material. When actuated, trigger assembly 40 activates the pump assembly 54 to generate a suction force capable of moving bodily fluids and/or UIM from the vessel, through the suction cannula 94 and into the barrel 56. Trigger assembly 40 is comprised of a trigger handle 41, grasp portion 16, an upper tab 46, and a lower tab 48. Trigger assembly 40 is connected to the plunger rod 44. Grasp portion 16 is configured to be held with by the user's fingers. The length of a grip area of grasp portion 16, identified as G on FIG. 6A, is selected to ensure the user can easily actuate the device using some or all fingers. In one embodiment, length G may be approximately 2.5-3.5 inches.

Figure 11:
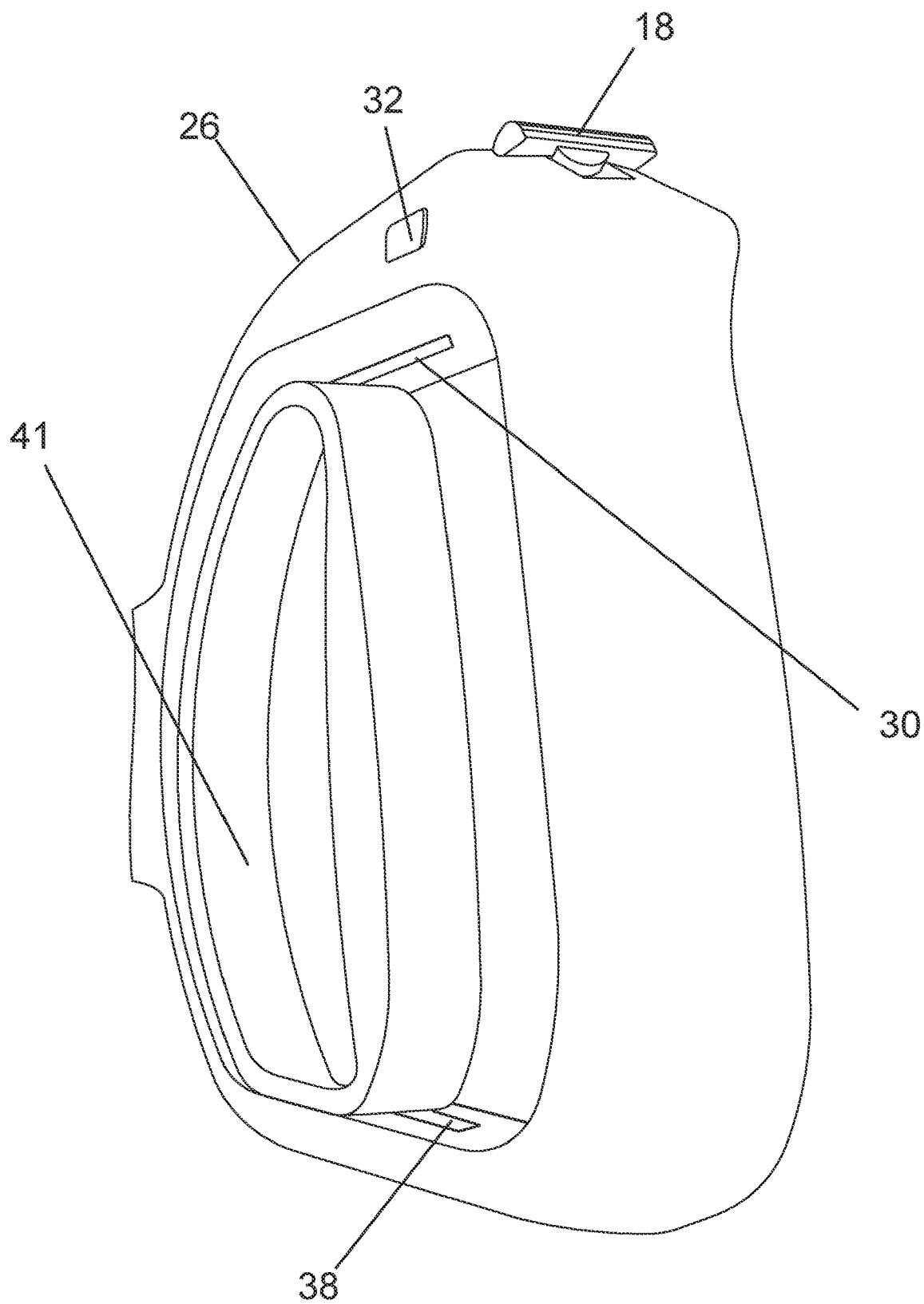
FIG. 11 illustrates a partial view of a handle subassembly in accordance with some embodiments.
Figure 12A:
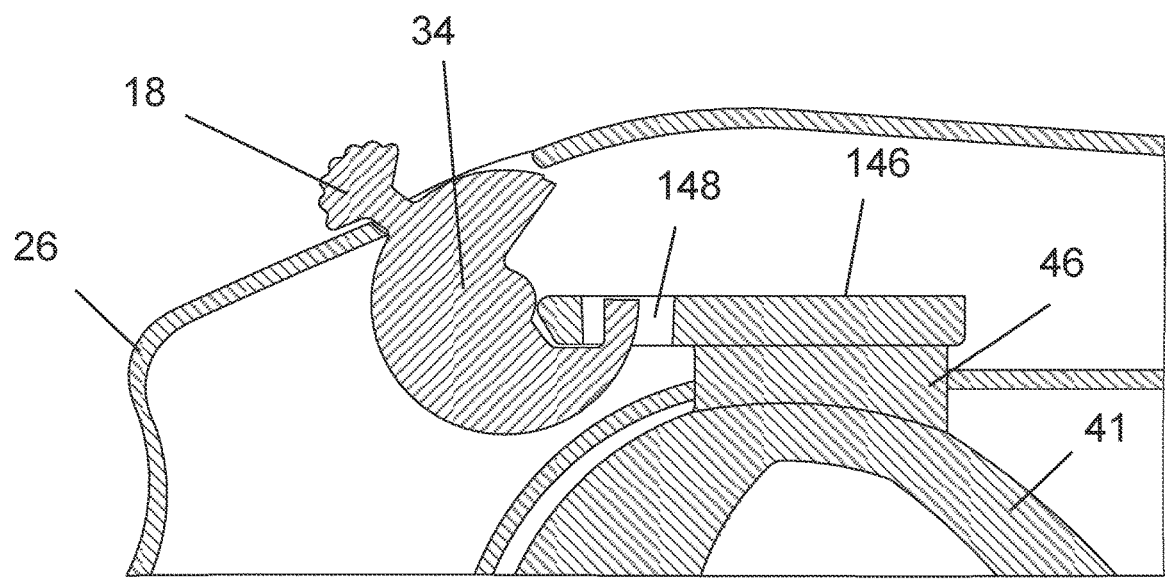
FIG. 12A and FIG. 12B illustrate partial cross-sectional views of a vacuum locking mechanism in accordance with some embodiments.
Figure 12B:
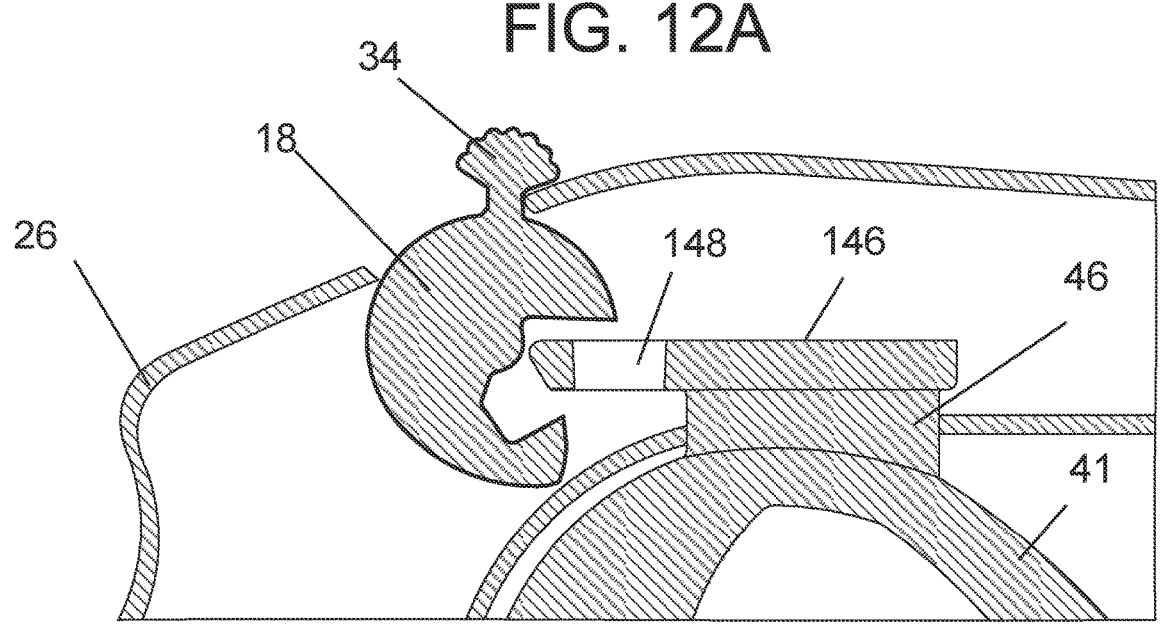

The upper tab 46 which is located on an upper portion of trigger assembly 40 and a lower tab 48 located on a lower portion of the trigger assembly 40, are received in the corresponding upper handle slot 30 and lower handle slot 38 of handle body 26 (as shown in FIG. 11). This arrangement guides the proximal and distal movement of the trigger assembly 40 relative to the handle body 26. Upper tab 46 comprises an upper vertical extension 144, a horizontal face 146, and a horizontal face opening 148. Horizontal face 146 is configured to interact with the volume limiter assembly and the horizontal face opening 148 is configured to interact with the vacuum locking mechanism 34 (as shown in FIGS. 12A-12B), as described in more detail below. When the user applies an activation force on trigger assembly 40 in a proximal direction the upper tab 46 and lower tab 48 of trigger assembly 40 slide proximally along and within the upper slot 30 and lower slot 38 of handle body 26. When the user releases their grip, the force generated by spring 64 is transferred to the trigger assembly 40, causing the upper tab 46 and lower tab 48 to slide distally within the upper slot 30 and lower slots 38; thereby returning the trigger assembly 40 toward the rest position.

Figure 4:
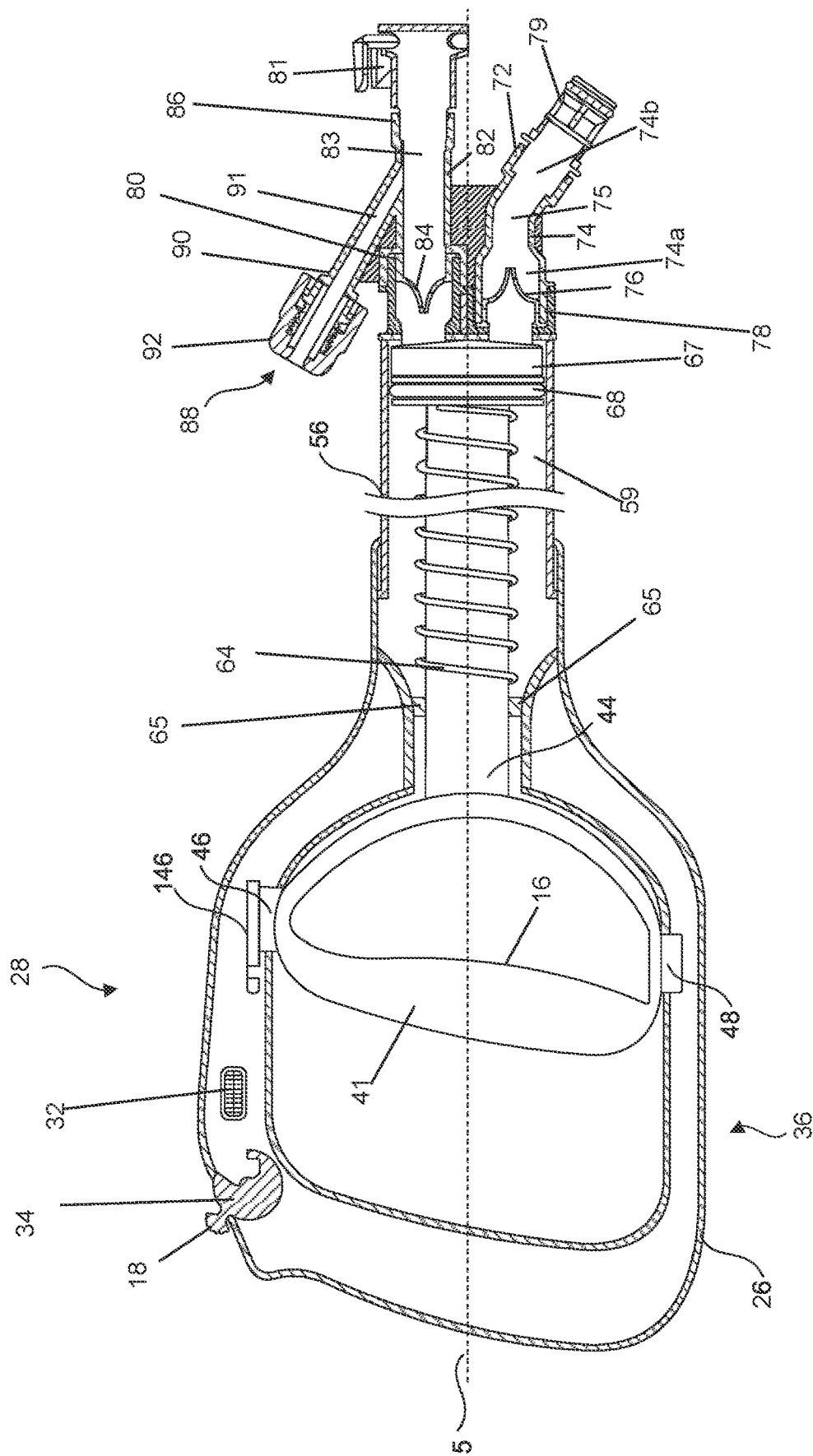
FIG. 4 illustrates a side view of an aspiration device in a resting position shown in partial cross-section in accordance with some embodiments.

When the trigger assembly 40 is in the resting position (as shown in FIG. 4) the plunger rod 44 is partially disposed within both the barrel cavity 59 and the handle body 26. Spring 64 is coaxially arranged around a portion of the plunger rod 44 and is also partially disposed within both the barrel cavity 59 and the handle body 26. To aspirate fluid and generate a suction force, the user grasps and pulls back (in a proximal direction) on grasp portion 16 of trigger assembly 40. This pulling back motion in a proximal direction generates a suction force as the plunger rod 44, spring 64, and plunger body 67 are longitudinally retracted within barrel 56 (as described in more detail below).

Figure 13:
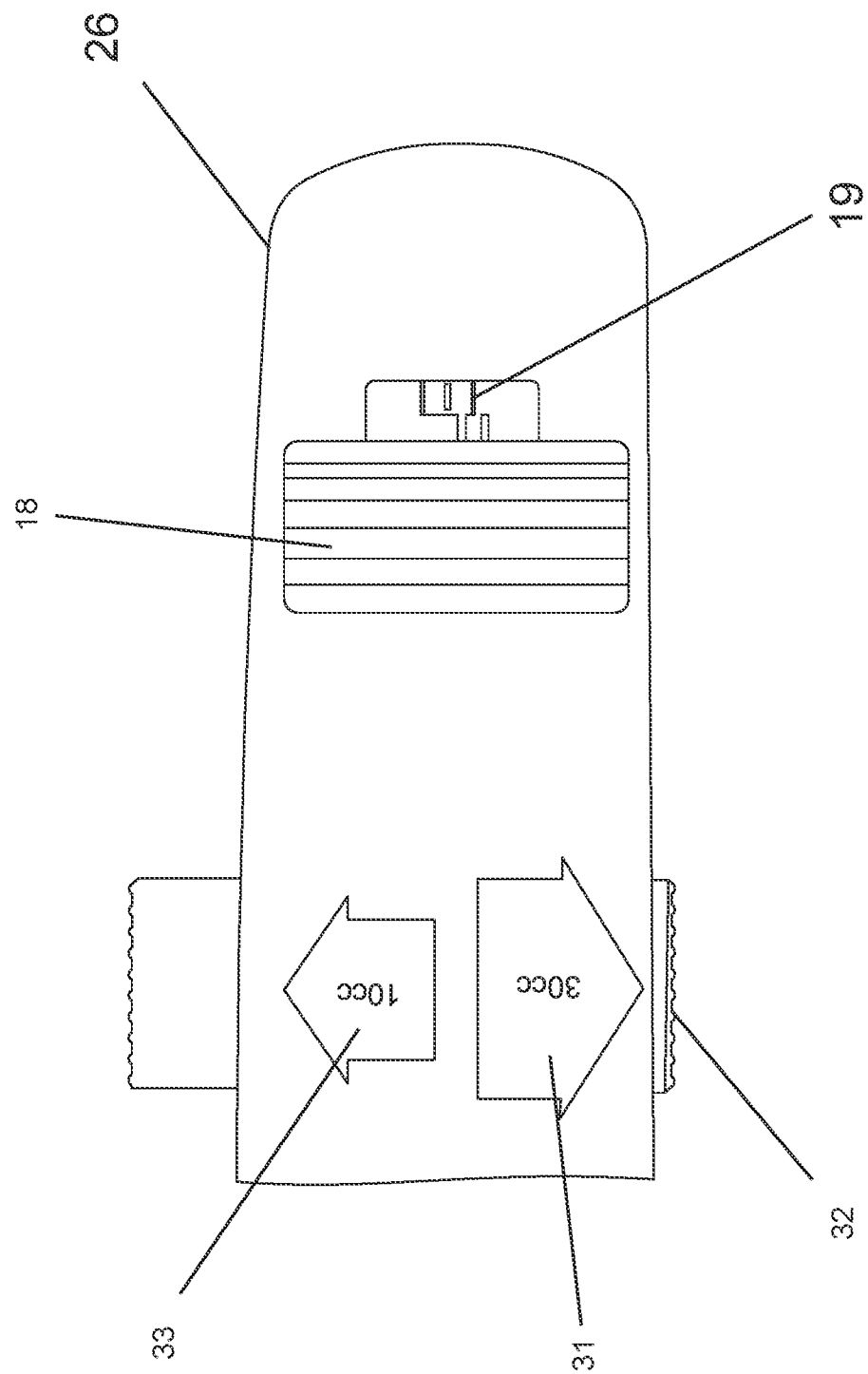
FIG. 13 and FIG. 14 illustrate partial top-down views of an aspiration device in accordance with some embodiments.
Figure 14:
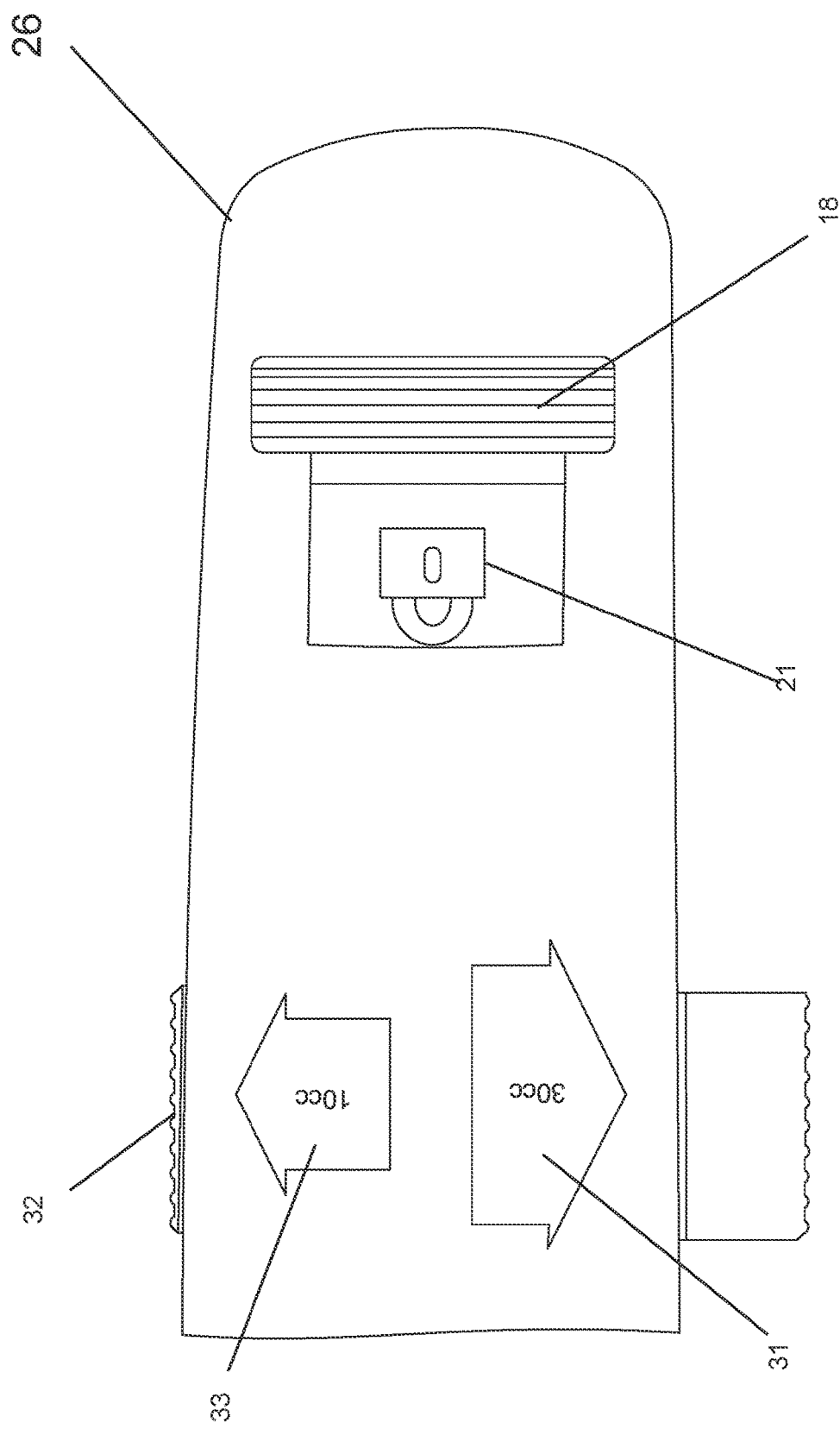

In one embodiment, the volume per trigger pull of aspirated fluid is controlled by a volume limiter element 32, which may be positioned on the handle body upper section 28 (as shown in FIG. 4). The volume limiter comprises a first fluid volume setting 31 and a second fluid volume setting 33 (as shown in FIGS. 13-14). The first fluid volume setting 31 and the second fluid volume setting 33 relate to the amount of bodily fluid to be removed from the patient during a single pull of the trigger assembly 40. In one embodiment, the first fluid volume setting 31 represents a larger volume (e.g., 30 cc) than the second fluid volume setting 33 (e.g., 10 cc). In another embodiment, the first fluid volume setting represents a smaller volume than the second fluid volume setting. The volume settings can be preselected for any volume setting that is equal to or less than the total volume capacity of the barrel cavity 59. The visual indicators 31, 33 comprise any of the following: numbers, letters, shapes, colors, or any other indicia known in the art. In some embodiments, activation and/or deactivation of the volume limiter may include a sound or other tactile feedback.

In one embodiment, a procedure may include a recommended maximum volume of blood that may be safely removed from a patient before transfusion or infusion is required. For example, in certain aspiration procedures to remove UIM known in the art may be a maximum volume of blood that can be safely removed during a single procedure. This maximum volume of blood that can be safely removed is often patient specific and depends on various patient characteristics including, but not limited to patient history, current medical condition, age, weight, or other known characteristics. By way of a non-limiting example the maximum volume of blood to be removed in the below example will range from 0 cc to 600 cc.

The volume limiter feature allows a user to select the specific volume to be aspirated in a single trigger pull as well as to change the desired volume per trigger pull at any time during the procedure. The volume limiter is comprised of a volume limiter actuator element 32 and travel stop. Travel stop may be formed as part of the actuator element 32 or as a separate element moveable into the travel path of the trigger 40. When the user engages the volume limiter actuator element 32, travel stop moves into the path of upper tab 46, preventing further proximal travel of trigger assembly 40 thereby limiting the volume of fluid which may be aspirated into barrel 56. In one example, the volume limiter actuator element 32 may have two settings, such as 10 cc and 30 cc. In other non-limiting embodiments, the volume limiter feature may have more settings, such as 10, 20, 30, 40, 50 cc.

The location of the volume limiter actuator element 32 allows the user to manipulate volume settings using the same hand that is holding the device 12. Single-handed volume setting changes may be accomplished by placing volume limiter actuator element 32 on the handle body side surface (as shown in FIGS. 13-14), or in another location on the handle 14 or trigger assembly 40. The location of the volume limiter actuator element 32 on the handle 14 allows a user to maintain force on the trigger 40 while manipulating the volume limiter actuator element 32 using his/her thumb or other finger without having to use two hands.

As described above, the volume limiter provides the user with the ability to control the amount of blood volume to be removed per trigger pull from the patient during a "search phase" of the procedure and an "active suction phase" of the procedure. The search phase of the procedure is when a user is pulling the trigger 40 to activate aspiration and generate a suction force (thereby removing blood from a patient) prior to the distal end of the suction cannula 94 (for example an expandable funnel 104 distal end) becoming engaged with the UIM. The active suction phase of the procedure is when the user has confirmed that the UIM is engaged with the suction cannula 94 distal end and pulls the trigger 40 to generate active suction force to remove the UIM from the patient's body and into the device.

The reason a user may be required to pull the trigger 40 during a search phase is that using only common medical imaging techniques known in the art the user may not be able to determine if the suction cannula 94 is properly placed and fully engaged with the UIM. If the suction cannula 94 is correctly positioned and engaged with the UIM during the search phase, the user will feel a tactile feedback in trigger assembly 40 indicating that the UIM has been engaged by the suction cannula 94. The tactile feedback is generated almost immediately as the vacuum or negative pressure increases, which in turn increases the suction force required to remove the UIM. Furthermore, as the user pulls on the trigger 40 to generate the suction force and engage the UIM, the force exerted on the trigger 40 by the increased negative pressure pulls the trigger 40 distally (i.e., the tactile feedback). This pull on the trigger 40 is therefore felt by user as a tactile feedback indicating to a user that the UIM has been successfully engaged with the suction cannula 94 and the procedure can now transition to the active suction phase. Once the UIM passes through the suction cannula distal end and fluid flow returns, the force required by user to pull the trigger 40 will decrease. In addition to a tactile feedback, the user may also receive a visual feedback from the system upon engagement with the UIM. For example, the user may visually notice a reduction (or a complete stop) in fluid flow through the system and into the barrel cavity 59 upon the UIM becoming engaged with the system.

In another embodiment (not shown), the system comprises a pressure gauge to provide additional feedback to the user. For example, the pressure gauge may be placed in fluid communication with the suction cannula, the barrel inlet channel, and/or the barrel cavity. The pressure gauge will measure any changes in pressure within the system. As described above, when the UIM is engaged with the system there may be an increase in vacuum or negative pressure, and this pressure change will be detected by the pressure gauge. The pressure gauge is configured to provide either an audio and/or visual feedback to the user to notify the user of this pressure change.

Any pulls of the trigger 40 during the search phase will remove a certain amount of volume of blood from the patient, thereby potentially reducing the number of trigger pulls available to the user during the active suction phase (as described in more detail below).

The use of a volume limiter feature solves this problem by reducing the total volume of blood removed per trigger pull during the search phase as compared to the total volume of blood removed per trigger pull during the active suction phase. By way of a non-limited example, the volume limiter may comprise a maximum volume setting of 30 cc and a minimum volume setting of 10 cc. If the volume limiter is engaged to the maximum volume setting then each pull of the trigger 40 will remove 30 cc of blood. If the total volume of blood that can be safely removed from the patient during a single procedure is 600 cc, the user would be limited to a total of twenty trigger pulls at the maximum volume setting (30 cc of blood removed per pull at twenty total pulls=600 cc of blood removed). If the user is required to do six trigger pulls during the search phase this would equal 180 cc of blood removed from the patient during the search phase alone; leaving only 420 cc of total blood volume that can be safely removed from the patient for remainder of the procedure. Once user has received the tactile feedback and/or otherwise confirms the UIM has been engaged with the suction cannula 94 and enters the active suction phase, the user would be limited to a total of fourteen trigger pulls to try and successfully remove the UIM. However, if during the search phase the user engages the minimum volume setting of 10 cc of the volume limiter and during the active suction phase the user then switches the volume setting and engages the maximum volume setting of 30 cc of the volume limiter, the total number of trigger pulls during the active suction phase is increased (as shown below in more detail). For example, if the user is required to do six trigger pulls during the search phase and has the volume limiter set to the minimum volume setting of 10 cc per pull, this would equal 60 cc of blood volume removed from the patient during the search phase alone; leaving 540 cc of total blood volume that is able to be safely removed for remained of the procedure. Once user has confirmed the UIM has been engaged with the suction cannula 94 and the procedure transitions to the active suction phase, the user changes the volume limiter actuator element 32 to the minimum volume setting of 10 cc per pull and the user would be limited to at least eighteen trigger pulls to try and successfully remove the UIM. Therefore, in this non-limited example by using the minimum volume setting of the volume limiter during the search phase of the procedure the user would gain an additional 4 trigger pulls during the active suction phase with the volume limiter actuator element 32 set to the maximum volume setting of 30 cc. These additional trigger pulls during active suction phase likely increases the chances of successfully removing the UIM substantially en bloc. Moreover, the volume limiter feature also allows the user the ability to switch between the minimum volume setting and the maximum volume setting at any time during the procedure, for example if user needs to "re-enter" the search phase during the procedure (e.g., if the UIM becomes disengaged or additional UIM in a second treatment site is required to be removed).

Table 1 below provides examples for an embodiment in which a maximum total blood volume of 600 cc can be removed from a patient during the procedure, and each trigger pull during both the search phase and active phase of the procedure aspirates a total blood volume of 30 cc:

| # Trigger Pulls During Search Phase | Total Blood Volume Removed during Search Phase | # of Trigger Pulls available during Active Suction Phase | Total Blood Volume Removed during Search Phase | Total Blood Volume Removed During Procedure |
|---|---|---|---|---|
| 1  | 30 cc  | 19 | 570 cc | 600 cc |
| 2  | 60 cc  | 18 | 540 cc | 600 cc |
| 3  | 90 cc  | 17 | 510 cc | 600 cc |
| 4  | 120 cc | 16 | 480 cc | 600 cc |
| 5  | 150 cc | 15 | 450 cc | 600 cc |
| 6  | 180 cc | 14 | 420 cc | 600 cc |
| 7  | 210 cc | 13 | 390 cc | 600 cc |
| 8  | 240 cc | 12 | 360 cc | 600 cc |
| 9  | 270 cc | 11 | 330 cc | 600 cc |
| 10 | 300 cc | 10 | 300 cc | 600 cc |
| 11 | 330 cc | 9  | 270 cc | 600 cc |
| 12 | 360 cc | 8  | 240 cc | 600 cc |
| 13 | 390 cc | 7  | 210 cc | 600 cc |
| 14 | 420 cc | 6  | 180 cc | 600 cc |
| 15 | 450 cc | 5  | 150 cc | 600 cc |
| 16 | 480 cc | 4  | 120 cc | 600 cc |
| 17 | 510 cc | 3  | 90 cc  | 600 cc |
| 18 | 540 cc | 2  | 60 cc  | 600 cc |
| 19 | 570 cc | 1  | 30 cc  | 600 cc |

Table 2 below provides examples for an embodiment in which a total blood volume of 600 cc can be removed from a patient during the procedure, and the volume limiter is set to a minimum volume setting of 10 cc per trigger pull during the search phase and a maximum volume setting of 30 cc per trigger pull during the active suction phase:

| # Trigger Pulls During Search Phase | Total Blood Volume Removed during Search Phase | # of Trigger Pulls available during Active Suction Phase | Total Blood Volume Removed during Search Phase | Total Blood Volume Removed During Procedure |
|---|---|---|---|---|
| 1 | 10 cc | 19 | 570 cc | 580 cc |
| 2 | 20 cc | 19 | 570 cc | 590 cc |
| 3 | 30 cc | 19 | 570 cc | 600 cc |
| 4 | 40 cc | 18 | 540 cc | 580 cc |
| 5 | 50 cc | 18 | 540 cc | 590 cc |
| 6 | 60 cc | 18 | 540 cc | 600 cc |
| 7 | 70 cc | 17 | 510 cc | 580 cc |
| 8 | 80 cc | 17 | 510 cc | 590 cc |
| 9 | 90 cc | 17 | 510 cc | 600 cc |
| 10 | 100 cc | 16 | 480 cc | 580 cc |
| 11 | 110 cc | 16 | 480 cc | 590 cc |
| 12 | 120 cc | 16 | 480 cc | 600 cc |
| 13 | 130 cc | 15 | 450 cc | 580 cc |
| 14 | 140 cc | 15 | 450 cc | 590 cc |
| 15 | 150 cc | 15 | 450 cc | 600 cc |
| 16 | 160 cc | 14 | 420 cc | 580 cc |
| 17 | 170 cc | 14 | 420 cc | 590 cc |
| 18 | 180 cc | 14 | 420 cc | 600 cc |
| 19 | 190 cc | 13 | 390 cc | 580 cc |
| 20 | 200 cc | 13 | 390 cc | 590 cc |
| 21 | 210 cc | 13 | 390 cc | 600 cc |
| 22 | 220 cc | 12 | 360 cc | 580 cc |
| 23 | 230 cc | 12 | 360 cc | 590 cc |
| 24 | 240 cc | 12 | 360 cc | 600 cc |
| 25 | 250 cc | 11 | 330 cc | 580 cc |
| 26 | 260 cc | 11 | 330 cc | 590 cc |
| 27 | 270 cc | 11 | 330 cc | 600 cc |
| 28 | 280 cc | 10 | 300 cc | 580 cc |
| 29 | 290 cc | 10 | 300 cc | 590 cc |
| 30 | 300 cc | 10 | 300 cc | 600 cc |
| 31 | 310 cc | 9 | 270 cc | 580 cc |
| 32 | 320 cc | 9 | 270 cc | 590 cc |
| 33 | 330 cc | 9 | 270 cc | 600 cc |
| 34 | 340 cc | 8 | 240 cc | 580 cc |
| 35 | 350 cc | 8 | 240 cc | 590 cc |
| 36 | 360 cc | 8 | 240 cc | 600 cc |
| 37 | 370 cc | 7 | 210 cc | 580 cc |
| 38 | 380 cc | 7 | 210 cc | 590 cc |
| 39 | 390 cc | 7 | 210 cc | 600 cc |
| 40 | 400 cc | 6 | 180 cc | 580 cc |
| 41 | 410 cc | 6 | 180 cc | 590 cc |
| 42 | 420 cc | 6 | 180 cc | 600 cc |
| 43 | 430 cc | 5 | 150 cc | 580 cc |
| 44 | 440 cc | 5 | 150 cc | 590 cc |
| 45 | 450 cc | 5 | 150 cc | 600 cc |
| 46 | 460 cc | 4 | 120 cc | 580 cc |
| 47 | 470 cc | 4 | 120 cc | 590 cc |
| 48 | 480 cc | 4 | 120 cc | 600 cc |
| 49 | 490 cc | 3 | 90 cc | 580 cc |
| 50 | 500 cc | 3 | 90 cc | 590 cc |
| 51 | 510 cc | 3 | 90 cc | 600 cc |
| 52 | 520 cc | 2 | 60 cc | 580 cc |
| 53 | 530 cc | 2 | 60 cc | 590 cc |
| 54 | 540 cc | 2 | 60 cc | 600 cc |
| 55 | 550 cc | 1 | 30 cc | 580 cc |
| 56 | 560 cc | 1 | 30 cc | 590 cc |
| 57 | 570 cc | 1 | 30 cc | 600 cc |

Therefore, the volume limiter provides the user with more control over the total maximum about of blood to be removed during a procedure and the ability to focus the maximum blood loss during the active suction phase (i.e., the more critical stage of the procedure).

Vacuum locking mechanism 34 (as shown in FIGS. 12A-14), is designed to be engaged by the user to maintain a constant vacuum (negative pressure) or a continuous suction force within the system without the user having to maintain continuous hand force or continuous pulling (in a proximal direction) on the trigger assembly 40. In one embodiment, the user engages the vacuum lock actuator 18 by applying a first force (i.e., in the proximal direction) upon the vacuum lock actuator 18 with a finger, and a second opposite force (i.e., in the distal direction) upon the vacuum lock actuator 18. The vacuum locking mechanism 34 further comprises a first vacuum locking visual indicator 21 to represent the vacuum locking mechanism 34 is engaged, and a second vacuum locking visual indicator 19 to represent the vacuum locking mechanism 34 is disengaged. The vacuum locking indicators 19, 21 comprise either a symbol (such as a lock and/or unlock), letters, colors, numbers, or another visual indicator.

During the active suction phase of the procedure the UIM may become occluded in the distal end of the suction cannula 94. For example, the user may visualize a reduced volume of aspirated blood through the system (for example, little or no visual bodily fluid is seen exiting the suction cannula 94 and/or into the barrel 56) but user still has a tactile feedback from the device 12 that the UIM is still engaged with the suction cannula 94. In this situation the user may activate the vacuum lock mechanism 34, and this advantageously allows the user to selectively lock the trigger assembly 40 in an active aspiration position, thereby maintaining a constant suction force or vacuum through the suction cannula 94 without requiring the user to physically pull on the trigger assembly 40. The vacuum lock mechanism 34 thereby aids in the usability of the device as the vacuum lock mechanism 34 allows a user to physically release the trigger assembly 40 but continue to maintain constant vacuum and constant section force upon the engaged UIM. The continuous vacuum and constant suction force on the UIM may be maintained for the period of time required to remove the UIM successfully en bloc. Using the vacuum lock feature 34 saves the user from physically pulling on the trigger assembly 40 for this entire time period, reducing a potential for user hand fatigue during the procedure.

In one embodiment, the vacuum locking mechanism 34 is ergonomically located on the handle body 26 so that the user can simultaneously maintain the trigger position and activate actuator 18 using a single hand. Engaging the locking mechanism may comprise a tactile feedback response such as a snapping noise, indicating to the user that the trigger may be released without loss of negative pressure.

In one embodiment (as shown in FIG. 12A) the vacuum locking mechanism 34 is in the engaged position and a capturing element 35 is engaged with the horizontal face opening 148 which locks the trigger assembly 40 position in a stationary place. When the user enables the locking mechanism 34 by pushing the vacuum lock actuator 18 in a distal direction, the vacuum locking mechanism 34 rotates proximally until a portion of capturing element 35 becomes positioned through the horizontal face opening 148 in the upper tab 46 of trigger assembly 40. Once engaged with the upper tab 46, the trigger assembly 40 is prevented from moving distally and the suction force is continuously maintained.

The vacuum locking mechanism 34 also comprises a disengaged position (as shown in FIG. 12B) in which the capturing element 35 is disengaged with the horizontal face opening 148 in the upper tab 46 of trigger assembly 40. When the vacuum locking mechanism 34 is in the disengaged position the trigger assembly 40 is freely movable in the proximal and/or distal direction and there is no longer a constant vacuum or suction force generated.

In another embodiment (not shown), vacuum locking mechanism may be "pre-locked". The user may activate the vacuum lock actuator at any time prior or during the procedure without actually immobilizing the trigger. The trigger will automatically lock in place only after it is in a fully retracted position, or the maximum travel distance of the device. Locking mechanism rotates when the user pre-locks the system, but capturing element does not engage until trigger assembly is fully retracted. At maximum travel, the distal portion of the capturing element becomes aligned with the opening in upper tab, locking the trigger assembly in place. One advantage of the pre-lock feature is that the user does not have to remember to activate the locking mechanism once the clot has been located and engaged. Instead, the user can just release grip from the trigger once negative pressure has been established and the vacuum locking mechanism will automatically engage.

In another embodiment (not shown), once UIM is engaged the user may alternatively connect the aspiration device to a secondary vacuum source that can generate a continuous suction/vacuum force. For example, the aspiration device may be used by the user during the search phase of the procedure only, and once the UIM has been engaged and user enters the active suction phase the suction cannula can be attached to a reinfusion circuit that comprises a pump capable of simultaneously generating a suction force and a drive force. Such a reinfusion circuit and pump is described in U.S. patent application Ser. No. 16/778,657, filed Jan. 31, 2020; and U.S. Pat. No. 8,075,510, filed Aug. 6, 2008, both of which are incorporated herein by reference.

The pump assembly 54 performs several functions including, but not limited to, generating the suction force and driving force necessary to aspirate and remove target UIM, providing a temporary repository for aspirated fluids, and activating and/or deactivating specific fluid flow pathways. The pump assembly 54 comprises a barrel 56, a spring 64, a plunger body 67, and a plunger rod 44. Barrel 56 is comprised of channels 60 and 62 which receive the barrel outlet valve 76 and barrel inlet valve 84. The plunger body 67 comprises a plunger body 67, and an O-ring 68. Handle tab 65 is configured to securely attach with (or otherwise engage with) a proximal end of the spring 64. A distal end of the spring 64 is securely connected to the plunger body 67. A proximal end of the plunger body 67 is securely attached to a distal end of the plunger rod 44. The O-ring 68 co-axially surrounds at least a portion of the plunger body 67 and is securely attached to an outer surface of the plunger body 67 (via an interference fit). The O-ring 68 and is configured to provide for a fluid tight seal between the plunger body 67 and an inner wall of barrel 56.

The maximum volume of the barrel 56 is configured to be at least the same volume of the suction cannula 94. It is within the conception of this disclosure that the maximum volume of the barrel 56 may be up to 50% more than the volume of the suction cannula 94, thereby ensuring that the barrel 56 can sufficiently clear the total volume of the suction cannula 94 during a single pull of the trigger 40.

The trigger assembly 40 is connected to the plunger rod 44, and proximal movement of the trigger assembly 40 is configured to result in proximal movement of the plunger rod 44, spring 64, plunger body 67, and o-ring 68, thereby creating a vacuum inside the barrel assembly 54 and generating a suction force through the system 10. Distal movement of the trigger assembly 40 is configured to result in distal movement of the plunger rod 44, spring 64, plunger body 67, and o-ring 68, thereby generating a drive force through system 10.

In one embodiment, the barrel 56 comprises a first outer barrel surface marking 57 that corresponds to a first volume setting (i.e., 30 cc) of the volume limiter and a second outer barrel surface marking 58 that corresponds to a second volume setting (i.e., 10 cc) of the volume limiter. The barrel 56 is comprised of a translucent material. The Barrel 56 receives aspirated fluid through inlet channel 60 and retains such fluid until it is discharged through outlet channel 62. Barrel 56 comprises a barrel cavity 59, a proximal barrel opening 61, and a distal barrel face 63. Extending from the distal barrel face 63 is a barrel inlet channel 60 and a barrel outlet channel 62. Securely positioned between (via an interference fit) the barrel inlet channel 60 and the cannula port proximal end 80 of the connector body 70 is the barrel inlet valve 84. Securely positioned between (via an interference fit) the barrel outlet channel 60 and the waste port distal end 72 of the connector body 70 is the barrel outlet valve 76. The barrel inlet valve 84 and the barrel outlet valve 76 are both on-way valves and are positioned in opposing directions. In one embodiment, the barrel inlet valve 84 may be placed and/or staggered in any location along the barrel inlet channel 60 or within the cannula port 82. Similarly, the barrel outlet valve 84 may be placed and/or staggered in any location along the barrel outlet channel 62 or the waste port 47.

Barrel cavity 59 is defined by distal barrel face 63 and a cylindrical inner barrel wall section. Plunger body 67 is slideably positioned within barrel cavity 59. The maximum barrel fluid capacity may be selected to correspond with the maximum volume capacity of the cannula, such that a single full retraction of the trigger handle 41 will completely clear the lumen.

The system is designed to prevent captured bodily fluid in barrel cavity 59 from free flowing or passively flowing into the lower pressure waste collection assembly 112, otherwise known as a syphoning effect. The reason this is a potential problem is that the free flowing or passively flowing of fluid into the waste collection assembly 112 will increase the total amount of blood removed from the patient. For example, the free flowing or passively flowing of fluid into the waste collection assembly 112 may be continuous during an entire procedure, meaning blood is being removed from a patient not only during search phase or active suction phase as described above. As discussed above it is an intention of this device to control the total volume of blood removed from a patient to prevent unwanted problems for the patient. To solve this problem, in one embodiment the barrel outlet valve 76 remains closed until a certain cracking pressure or a predetermined pressure threshold is reached. In this embodiment, the barrel outlet valve 76 predetermined cracking pressure would be high enough to withstand normal blood pressure or at least 30 mm of mercury. When pressure drops below the predetermined cracking pressure, the barrel outlet valve 76 closes to prevent the unwanted backflow or passive flowing of fluid into the waste collection assembly 112. In another embodiment, the passive leaking of fluid through the barrel outlet valve 76 is controlled by ensuring as the spring 64 exerts a sufficient spring force onto the plunger rod 44 and plunger body 67 such that the sealing cap 47 engages to proximal most end of the barrel inlet channel 60 and a proximal most end of the barrel outlet channel 62 thereby ensuring a proper seal is created. Furthermore, the sealing cap 47 comprises a durometer (i.e., between 20 A to 70A) sufficient to engage with and seal the proximal most end of the barrel inlet channel 60 and a proximal most end of the barrel outlet channel 62.

Barrel inlet valve 84 opens in response to the negative pressure and/or suction force created in the barrel cavity 59 when trigger 40 is retracted in a proximal direction and the pump assembly 54 is activated. Any fluid within the suction cannula 94 assembly and/or near the distal end of the suction cannula 94 will be drawn into the barrel cavity 59. Barrel outlet valve 76, positioned in the opposite direction as the barrel inlet valve 84, opens in response to the generation of positive pressure and/or a driving force within the barrel cavity 59 caused by the forward or distal movement of the trigger 40.

Fluid flow through the system may also be controlled using any valve that limits fluid flow to a single direction including, but not limited to, pressure-activated valves such as duckbill, umbrella, dome, slit valve, or ball seating designs. Mechanically activated valves are also within the scope of this disclosure.

Figure 9:
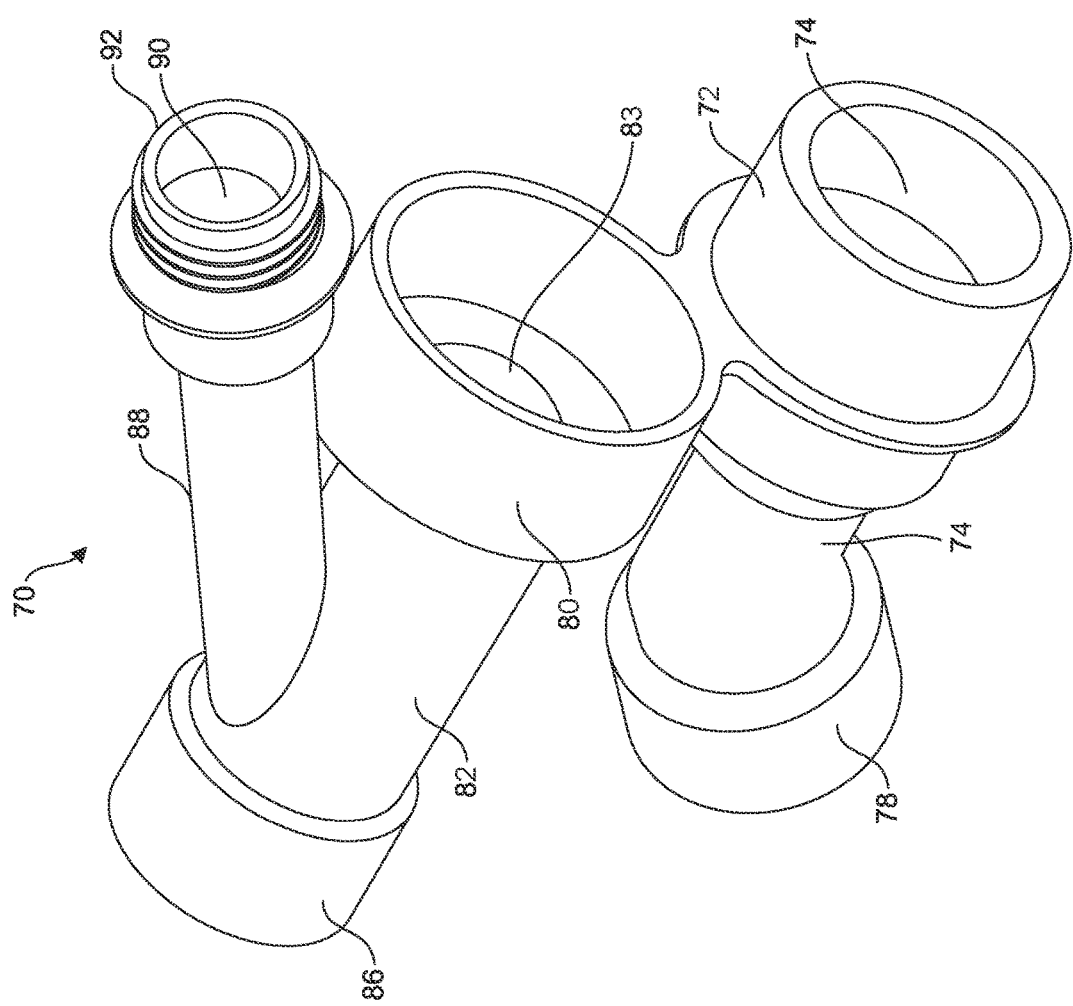
FIG. 9 illustrates a view of a connector body in accordance with some embodiments.
Figure 10:
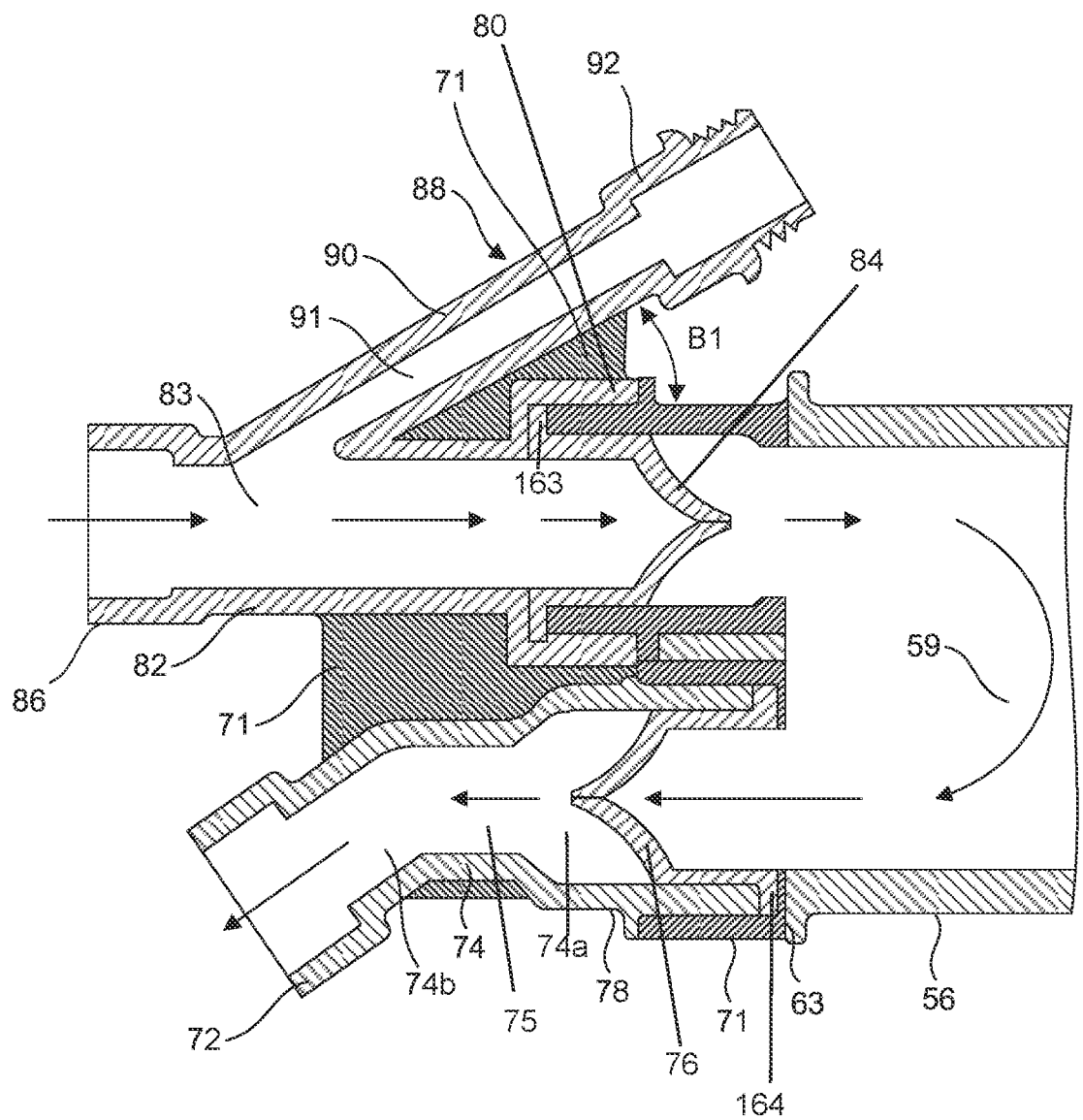
FIG. 10 illustrates a side cross-sectional view of a connector body in accordance with some embodiments.

Connector body 70 (as shown in FIG. 9) provides fluid pathways to and from the barrel 56 as well as providing access for accessory procedural tools and fluids. Connector body 70 comprises an ancillary port 88, ancillary port lumen 90, ancillary port adapter 92, a cannula port 82, a cannula port lumen 83, a cannula port proximal end 80, a cannula port distal end 86, a waste port 74, a waste port proximal end 72, a waste port lumen 75, a waste port proximal end 79, and a connector base 71. The proximal portion of connector body 70 is securely coupled to barrel 56. In one embodiment, connector body 70 is of unitary structure. In another embodiment (not shown), connector body may be comprised of individual port structures coupled together by connector base or other known connecting mechanism. In another embodiment (not shown), connector body does not include connector base. The waste port 74 is positioned in relation to the other port connections such that gravity will aid in the flow of UIM removed from the body through the waste port 72 and into the waste collection assembly 112.

Cannula port lumen 83 provides a dedicated fluid pathway from suction cannula 94 to barrel 56. Cannula port proximal end 80 is sized to mate with barrel inlet channel 60 of barrel 56 such that an outer flange 163 or an annular support member of the barrel inlet valve 84 is securely retained therebetween. In one embodiment (as shown in shown in FIG. 10), the distal end of barrel inlet channel 60 compresses the outer flange 163 or an annular support member of the barrel inlet valve 84 against an annular ledge of cannula port proximal end 80. The cannula port distal end 86 is securely connected to cannula port connector 81. In use, cannula port connector 81 couples to and is in fluid communication with the suction cannula 94, thus establishing a fluid pathway between a target site and barrel 56. When a vacuum, negative pressure, and/or suction force is generated, barrel inlet valve 84 opens to allow fluid to flow (represented by arrows in FIG. 10) from the suction cannula 94 through cannula port lumen 83 and into barrel cavity 59.

Waste port lumen 75 provides a dedicated fluid pathway from suction barrel 56 to the waste assembly 112. Waste port proximal end 72 is sized to mate with barrel outlet channel 62 of barrel 56 such that an outerflange 164 or an annular support member of the barrel outlet valve 76 is securely retained therebetween. The distal end of barrel outlet channel 62 compresses the outer flange 164 or an annular support member of the barrel outlet valve 76 against an annular ledge of waste port proximal end 72. The waste port distal end 78 is securely connected to waste port connector 79. In use, waste port connector 79 couples to and is in fluid communication with the waste collection assembly tubing 118, thus establishing a fluid pathway between a barrel cavity 59 and waste assembly 114. When a drive force is generated, barrel outlet valve 76 opens to allow fluid to flow (represented by arrows in FIG. 10) from the barrel cavity 95 through waste port lumen 75 and into waste assembly 114.

In one embodiment, the waste port connector 79 and cannula port connector 81 are of different dimensions to prevent the operator from inadvertently connecting the suction cannula 94 to waste port connector 79 and/or the waste collection tubing 118 to the cannula port connector 81.

Ancillary port 88 provides access to the treatment site for insertion and removal of ancillary devices such as secondary treatment devices (as described in more detail below), balloon catheters, angiographic catheters, embolic protection devices, wires and the like. Ancillary port 88 may also be used to deliver fluids such as saline, thrombolytic agents, contrast media, and/or other medicine. Additionally, ancillary port 88 may be used to insert a secondary device (as described below in more detail), or a secondary suction cannula (e.g., secondary suction catheter comprising a second expanding funnel and a cannula shaft with a smaller French size than cannula 94) to aid in the removal of the UIM through the ancillary port 88. Ancillary port 88 is comprised of an ancillary port adapter 92, ancillary port lumen 90 extending from the port adapter 92 to the cannula port inflow lumen 83. Ancillary port adapter 92 may be a luer-type fitting with sealing element to prevent the inadvertent introduction of air into the system through the ancillary port lumen 90, a quick connect style fitting, or any other fitting as known in the art.

The location and orientation of ancillary port 88 on aspiration device 12 facilitates ease of use during the procedure. In one embodiment (as shown in FIG. 9) ancillary port adaptor 92 faces proximally toward the user, so as to provide easy access by the operator at any time during the procedure, even when gripping the trigger 40 with one hand. In addition, ancillary port lumen 90 is offset from a longitudinal axis 5, as shown as angle "B1", to facilitate introduction to and withdrawal from cannula port lumen. In one nonlimiting aspect, angle B1 is approximately 45-55 degrees and may range from 10 to 70 degrees. In one aspect, ancillary port 88 height as measured from an outer wall of the barrel 56 to the ancillary port adapter 92 opening is approximately 1 inch and range up to 3 inches.

Figure 5:
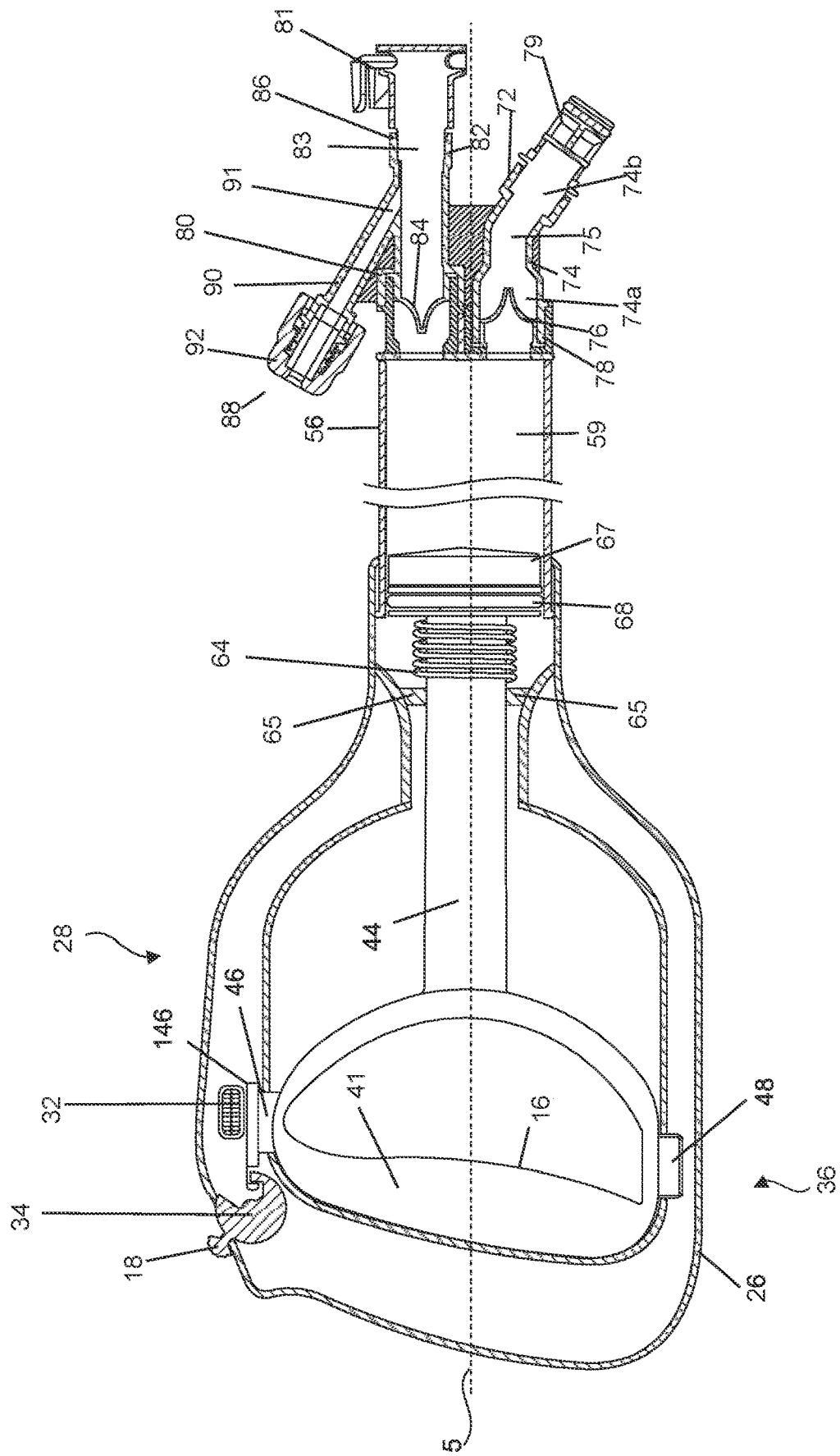
FIG. 5 illustrates a side view of the aspiration device of FIG. 4 in a fully retracted position.

The location and orientation of waste port 74 is specifically designed to facilitate ease of use and safety of the device during the procedure. Waste port 74 comprises a first waste port channel segment 74a and a second waste port channel segment 74b (as shown in FIGS. 4-5). The first waste port channel segment 74a is configured to be aligned substantially parallel to longitudinal axis 5 of device 12. second waste port channel segment 74b is offset from longitudinal axis 5, extending distally in a downward direction. In one nonlimiting aspect, the second waste port channel segment 74b is offset from longitudinal axis 5 between 0 degrees to 180 degrees, and approximately 30 degrees to 50 degrees relative to the longitudinal axis 5.

The waste port connector 79 is spatially separated from barrel 56, cannula port 83, and ancillary port 88, which provides several advantages to the user. The user has additional space to maneuver when establishing a connection between the suction cannula assembly 94 and barrel 56 as well as facilitating easy and quick connection to the waste connection system 112. Any waste or undesirable material passing from the barrel 56 will flow in a direction away the patient and the user's work area. In yet another advantage, UIM and other debris will pass en bloc and more freely through a gradually angled lumen than through a channel having an abrupt angle, an obtuse or right angle.

Figure 17:
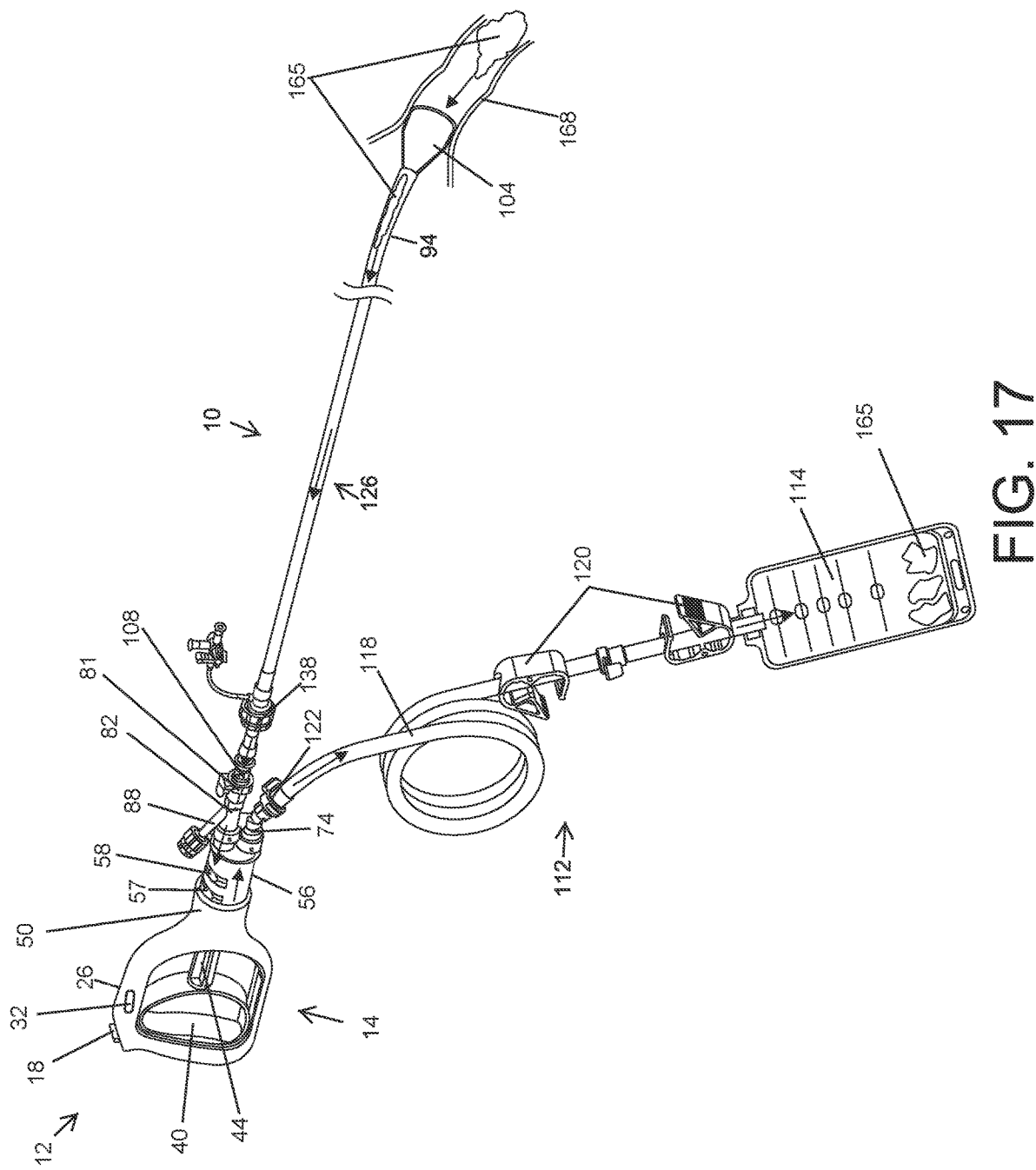
FIG. 17 illustrates the movement of undesirable material through an aspiration system in accordance with some embodiments.

Waste collection assembly 112 (as shown in FIG. 1 and FIG. 17) receives and temporarily stores fluid and debris (such as removed UIM 165) from aspiration device 12.

Waste collection assembly 112 comprises a waste connector 122, waste collection assembly tubing 118, pinch clamps 120, and waste collection receptacle 114. When waste collection assembly connector 122 is coupled to waste port connector 79, a fluid pathway is established between barrel 56 and waste collection receptacle 114. Fluid and debris will flow through the waste collection assembly tubing 118 and into waste collection receptacle 114. In the event that the waste collection receptacle 114 becomes full or otherwise needs replacement, pinch clamps 120 are provided to temporarily block fluid flow through waste collection assembly tubing 118. Once a new waste collection receptacle 114 has been connected, pinch clamps 120 are opened to restore flow through waste collection assembly tubing 118.

Figure 15:
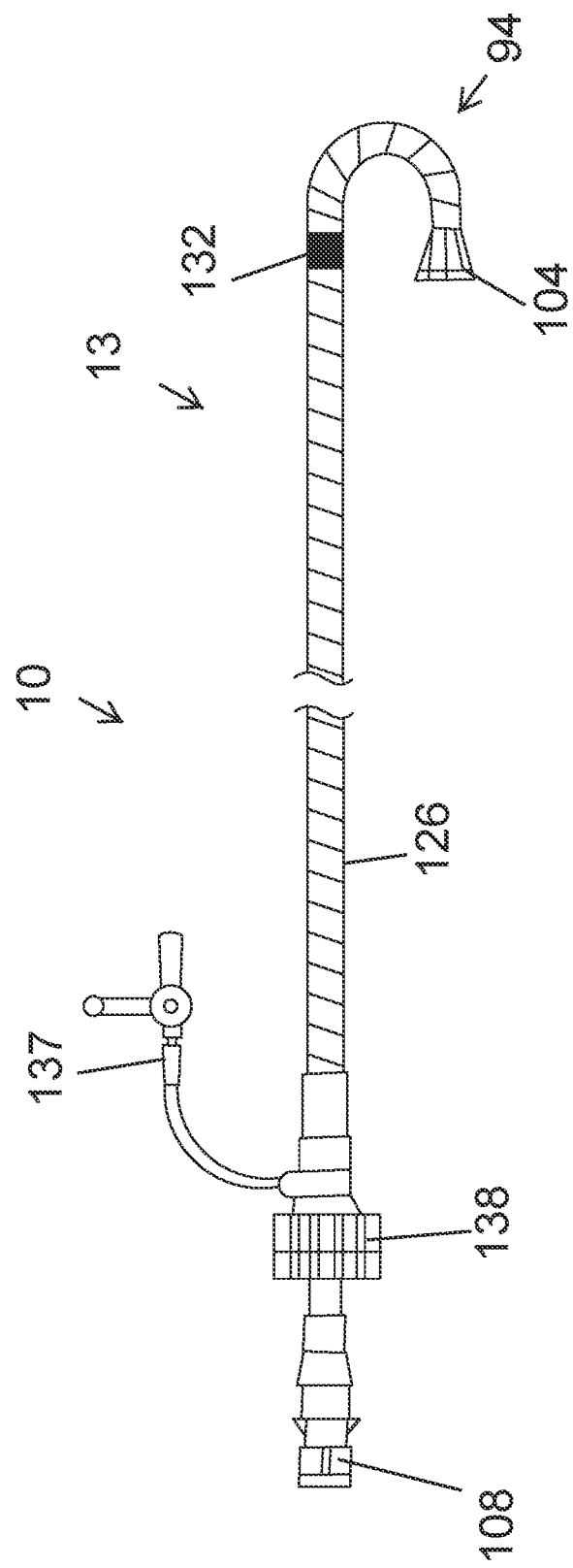
FIG. 15 illustrates a view of a suction cannula/sheath subassembly in accordance with some embodiments.
Figure 16:
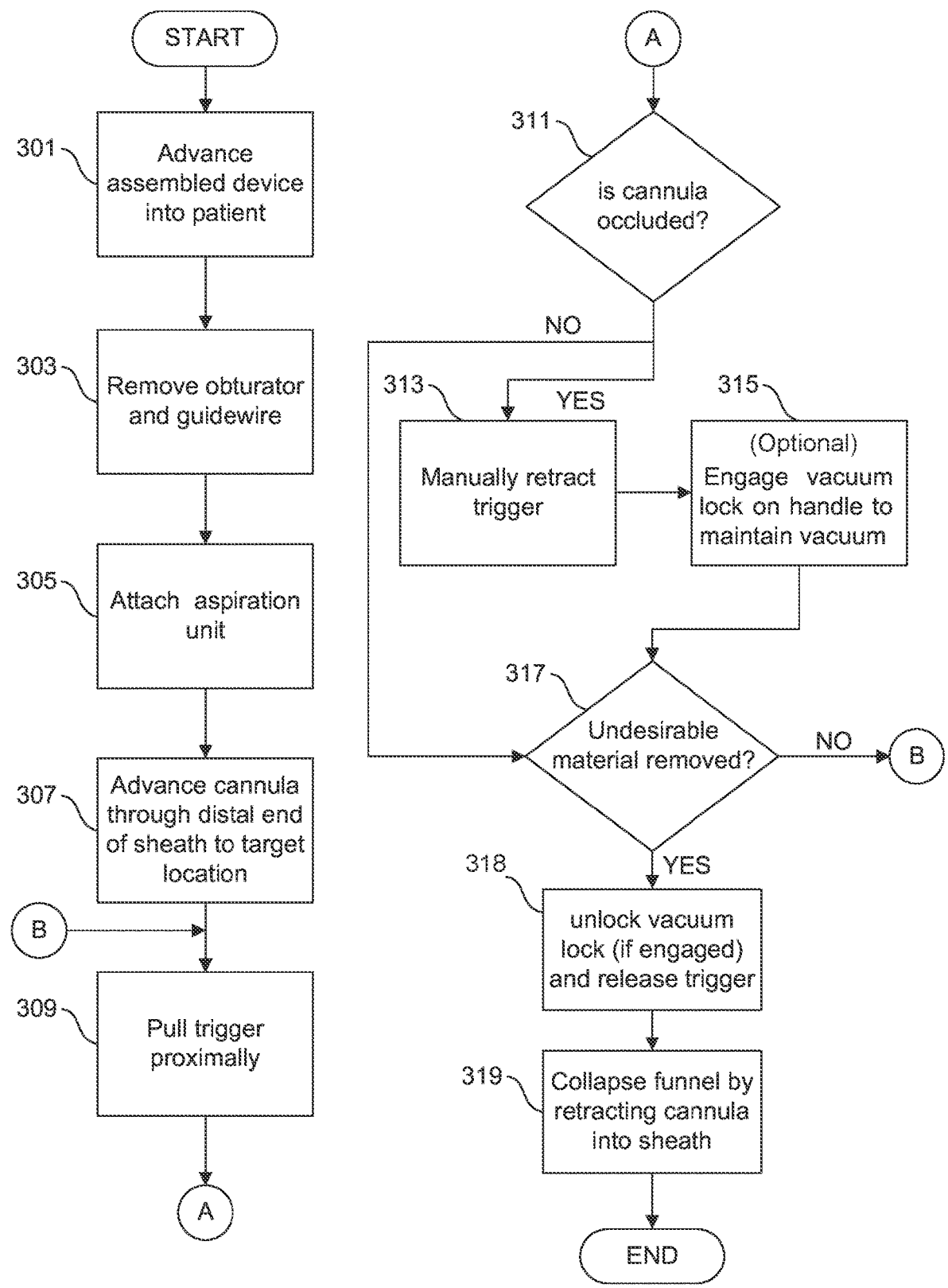
FIG. 16 illustrates a method of aspirating undesirable material in accordance with some embodiments.

Suction cannula 94 (as shown in FIG. 15) comprises a cannula proximal connector 108, an elongate cannula shaft 96 defining a cannula lumen, and a cannula distal tip section. In one embodiment, the cannula distal tip section comprises an expandable funnel 104. In another embodiment (not shown), the cannula distal tip section comprises a non-expandable member. An aspiration fluid pathway between the treatment site and barrel 56 is established by operatively coupling the cannula's proximal connector 108 to cannula port connector 81.

Elongate cannula shaft 96 comprises cannula lumen extending from cannula proximal connector 108 to cannula distal tip section. In one embodiment (not shown), cannula shaft may be comprised of additional lumens which may extend for a selected distance within or co-axially along cannula shaft, such that cannula may be a unitary or multi-layer structure. For example, the additional lumens may be used to gain access for a guidewire, secondary device (as described in more detail below), or any other medical device to the treatment site, while simultaneously creating a suction force through the cannula lumen on the UIM. In one embodiment, cannula shaft 96 may reinforced for enhanced cannula pushability, trackability and/or maneuverability during advancement through the vessel. Such reinforcement may include one or more stiffening elements positioned between and/or around individual shaft layers or embedded within a cannula shaft 96 layer. Reinforcement elements may be in the shape of a coil, weaved material or other patterns. The entire length or selected portions of cannula shaft 96 may be reinforced. In one embodiment, the working length of the cannula shaft 96 may be from approximately 5 cm to 200 cm to accommodate a range of vessel lengths.

The cannula distal tip section of cannula shaft 96 may be pre-shaped to form an angle or curve such that when unconstrained, the expanding funnel 104 becomes offset from the shaft's longitudinal axis (as shown in FIGS. 1, 15, and 17). The offset may be between 10 and 180 degrees. The shaped tip section profile may be formed through standard heat shaping techniques or by utilizing reinforcement elements previously described. The curved tip section is advantageous when the engaging a UIM which is partially or fully attached to a vessel wall and when the UIM is located in tortuous or difficult to reach vasculature, such as in a heart chamber or in a pulmonary vasculature.

In one embodiment, the cannula distal tip section comprises an expandable funnel 104 for engaging and moving UIM into lumen of suction cannula 94. The structural aspects of the funnel 104 including length, profile, structure and flexibility are designed to maximize en bloc clot retrieval while minimizing vessel damage. Funnel 104 has an unexpanded or compressed configuration and an expanded configuration. When in an unexpanded state, funnel 104 may have an outer diameter roughly equivalent to the diameter of cannula shaft 96. In the expanded configuration funnel 104 forms a substantially conical shape with the distal most funnel opening having a diameter larger than the cannula shaft diameter. In one embodiment, the diameter of the funnel opening when fully expanded is approximately 14 mm. The diameter of the funnel 104 may be dictated by the diameter of the target vessel. For example, various sized cannulas 94 comprises varying sized funnel 104 distal ends can be used in combination with the system 12 described here. The wall of funnel 104 may formed from the cannula shaft 96 or may be comprised of impermeable or semi-impermeable material. The funnel 104 may be self-expanding or mechanically actuated. In one embodiment, the funnel may include a plurality of expandable and independent struts or arms, encased, or otherwise attached to a semipermeable or impermeable membrane layer. Several embodiments of suction cannula 96 are described in more detail in U.S. patent application Ser. No. 16/778,657, filed Jan. 31, 2020, which is incorporated herein by reference.

In one embodiment (as shown in FIG. 1 and FIG. 15), the system 10 may comprise a procedural sheath 126 to be operatively coupled to suction cannula 94. When coaxially arranged with suction cannula 94, procedural sheath 126 facilitates insertion and advancement of cannula 94. Procedural sheath 126 may also be used to collapse and expand a self-expanding funnel 104 by longitudinal movement of either the sheath 126 and/or cannula 94. Procedural sheath 126 is comprised of a procedural sheath proximal hub 136 comprising a procedural sheath side port 137, and an elongated procedural sheath shaft defining a procedural sheath through lumen which terminates at a procedural sheath end section 132. In one embodiment, procedural sheath proximal hub 136 includes a sealing mechanism which prevents fluid backflow. In another embodiment, procedural sheath proximal hub 136 includes a mechanism 138 to lock and unlock the position of suction cannula 94 relative to the procedural sheath 126. When unlocked, suction cannula 94 may be longitudinally moved relative to the procedural sheath 126 and reposition suction cannula 94 relative to the UIM. Procedural sheath proximal hub 136 may be a touhy borst fitting or known fittings.

A method of using aspiration system 10 will now be described. In general, the method comprises prepping the patient and system components, accessing the targeted anatomical structure (such as a vessel 168), inserting and advancing suction cannula 94 toward the targeted UIM 165, attaching aspiration device 12, engaging and extracting the UIM 165, and removing device 12 from the patient. Although these method steps will be described with specific reference to vascular structures and specific ancillary devices, other anatomical structures and devices are within the scope of methods described herein. In some embodiments, other ancillary devices (such as secondary devices as described herein) and associated methods of use may be used with aspiration system 10.

The patient is first prepped using sterile technique. Access to the target vessel 168 or other target site is obtained using percutaneous or surgical techniques known in the art. A guidewire may be inserted to maintain access. The user next prepares the suction cannula/sheath subassembly 13. If desired, an optional obturator may be inserted into the cannula lumen to facilitate introduction into the vessel or other target location. Aspiration device 12 is prepped by setting the desired volume limit, closing the ancillary port 88, and removing any air present in the device 12. The waste collection assembly 112 is connected to the waste port connector on the aspiration device 12.

Funnel 104 of suction cannula 94 should be closed in an unexpanded state or collapsed state before inserting into the target vessel or other anatomical lumen. In one non-limiting method step, the user first loosens locking mechanism 138 of procedure sheath 126 allowing the cannula shaft 96 to slide freely co-axially within sheath lumen. The user then retracts cannula shaft 96 proximally until funnel 104 is fully enclosed and collapsed within shaft of the procedure sheath 126. To maintain the funnel 104 in a collapsed position during insertion into the vessel, the procedural sheath 126 hub locking mechanism 138 is retightened, locking the cannula shaft 96 in place against the procedural sheath 126. An obturator (not shown) may then be inserted into the cannula lumen, advanced and secured in place by connecting proximal cannula hub 108 and the obturator hub together. The subassembly 12 may be flushed via the obturator hub, procedural sheath side port 137, and/or ancillary port 88.

Referring to step 301, the user advances the obturator, procedural sheath/suction cannula subassembly 13 into the patient. In one embodiment, the user may flush the obturator with saline to increase lubricity. Once the obturator, procedural sheath 126, and suction cannula 94 subassembly are positioned within the target vessel at step 301, then the obturator and guidewire are removed at step 303 from the patient, leaving the cannula 94 in place. Once the obturator has been removed, the user may attach aspiration device 12 to the cannula 94 by attaching the cannula proximal connector 108 to cannula port inflow connector 81 of the device at step 305.

The system is then primed by opening an accessory port of the aspiration device to provide for blood bleed back; closing the accessory port; setting a volume limiter of aspiration device to a first volume setting; tilting the handle; and pulling the trigger.

The suction cannula/sheath assembly 13 is advanced through the vasculature and navigated to the desired location. In one embodiment, the funnel 104 of suction cannula 94 is advanced through a distal end of the procedural sheath 126 at step 307. In one embodiment, the suction cannula/sheath assembly 13 is advanced up to 20 cm proximal to the UIM prior to priming the system and expanding the funnel 104 (as described in more detail below). The funnel 104 may extend a select distance distally beyond the distal most end of the procedural sheath 126. In one embodiment, the select distance the funnel 104 may extend distally beyond the distal most end of the procedural sheath 126 may be up to 50 cm. In another embodiment, the select distance the funnel 104 may extend distally beyond the distal most end of the procedural sheath 126 may be up to 15 cm if the cannula 94 has a pre-shaped bend or curve (as described above); thereby preventing the procedural sheath 126 from resting on this per-shaped bend or curve.

The funnel 104 is placed in the expanded state by loosening the procedure sheath hub locking mechanism 138 and advancing the cannula 94 a selected distance beyond the distal opening of the procedure sheath 126. The procedure sheath hub locking mechanism is retightened to lock the cannula 94 in place, such that no air can enter the system and to longitudinal and/or coaxial movement of the cannula relative to the procedure sheath 126.

To begin the step of aspirating, the user manually pulls trigger handle 40 a select distance in the proximal direction at step 309 to activate the pump assembly 54. Manually pulling trigger handle 40 generates a negative pressure, vacuum, and/or a suction force within the barrel cavity 59, the barrel inlet channel 60, the barrel inlet valve 84, the cannula through lumen 98, cannula distal tip section, and within the target vasculature. The negative pressure, vacuum, and/or a suction force draws fluid from the target vasculature, through the cannula distal tip section, the cannula lumen, and into the barrel cavity 59. Manually releasing of the trigger 40 by the user will cause the spring force generated by spring 64 to move the trigger 40 and vacuum generating assembly 54 a selected distance in the distal direction, thereby generating an opposite positive pressure or a driving force within the barrel cavity 59. The positive pressure or driving force within the barrel cavity 59 will cause any fluid held in the barrel cavity 59 to be forced through the barrel outlet channel 62, the barrel outlet valve 76, through the waste collection assembly tubing 118, and into the waste collection assembly 112.

The user repeats trigger pull cycles until the UIM has either been successfully removed from the patient at step 317 or it has become engaged by and is occluding the funnel at step 311. The user is able to confirm the UIM has become engaged by and is occluding the funnel at step 311 as a result of the tactile feedback response felt by the resistance of the trigger movement and/or visual feedback response of seeing a decrease in fluid flow into the barrel cavity 59.

Engagement of the UIM may be confirmed using fluoroscopic or other imaging techniques. As an example, imaging contrast media may be delivered through an angiographic catheter which has been placed through cannula lumen using the ancillary port 88 of the device 12. As the UIM is aspirated and pulled or drawn into the cannula 94, the UIM may totally occlude or otherwise engage with the funnel 104 distal opening. Occlusion of the cannula may be indicated by a sudden increase in trigger resistance and/or tactile feedback (as described in detail above) felt by the user, and/or visual feedback seen by the user. At this point the user fully retracts trigger 40 at step 313 to apply maximum negative pressure against the UIM.

If the cannula distal tip section is fully occluded with the UIM then each manual trigger pull will gradually increase the negative pressure, vacuum, and/or suction force within the cannula 94 and specifically the suction force applied to the occluded/engaged UIM. This gradual increase of negative pressure, vacuum, and/or suction force (ex., −10 psi, −10.5 psi, −11 psi, −11.5 psi. −12 psi . . . ) occurs because the barrel inlet valve 84 is a one-way valve and maintain the negative pressure, vacuum, and/or suction force even as the trigger is released and each cycle is restarted. For example, if the cannula distal tip section is fully occluded with UIM and the trigger is released any trapped air or fluid in barrel will escape through the one-way barrel outlet valve 76; while the one-way barrel inlet valve 84 will remain closed and thereby maintaining the suction force on the UIM. As user pulls the trigger to activate additional suction forces or additional pull cycles the one-way barrel outlet valve 76 will remain closed and only the one-way barrel inlet valve 84 will open to provide this gradual increase of negative pressure, vacuum, and/or suction force on the UIM and help aid in the compression and removal of the UIM substantially en bloc. The UIM 165 compresses and elongates as it is drawn en bloc into the funnel 104 and through the cannula lumen. Moreover, mechanical clot compression may also be achieved by withdrawing the cannula 94 into the procedural sheath 126 causing the UIM-laden funnel 104 to collapse inside the procedure sheath 126. The UIM 165 is thus compressed and elongated by the combination of suction force and compression force by the collapsed funnel. Once the UIM has been captured by the suction cannula 94, the user may continue to manually aspirate fluids by repeating trigger pull cycles until the UIM has been completely removed from the target site, i.e., continuously repeating step 313.

Alternatively, at step 315 user may optionally activate the vacuum lock mechanism 34 feature after the UIM has been engaged by the funnel 104 and the trigger 40 has been manually retracted. This will maintain a vacuum or suction force without the user having to physically hold the trigger 40 in the retracted position. The vacuum or suction force is held until the UIM is drawn or pulled (substantially en bloc) into the funnel 104, through the cannula lumen, the barrel inlet channel, the barrel inlet valve 84, and into the barrel cavity 59. Once substantially all of the target UIM 165 has been extracted (if the vacuum lock mechanism was engaged it can now be released at step 318), the expanding funnel 104 is collapsed by retracting the cannula into procedure sheath 126 at step 319. The suction cannula/sheath assembly 13 can then be removed from the patient.

During the aspiration procedure, the total extracted fluid volume may be monitored using the barrel volume (adjusted if the volume limiter is used) combined with the number of pull cycles and/or by observing fluid volume of the waste bag volume indicators 116. If the waste collection receptacle 114 becomes full prior to finishing the procedure, it may be replaced by simply closing pinch clamps 120 on the waste collection assembly tubing, disconnecting the waste collection receptacle 114 from the waste collection assembly connector, attaching a new waste collection receptacle 114 and opening the pinch clamps 120 to reestablish the fluid flow.

In another embodiment (not shown), the handle and trigger assembly may be in the shape of a pistol grip comprises a pistol shaped handle and a pistol shaped trigger. In this embodiment, an integral waste reservoir capable of single-handed activation may be provided. In this embodiment the user would only need to use one or two fingers on the pistol shaped trigger to activate aspiration or the suction force and the drive force. This embodiment also comprises a barrel, spring, plunger rod, plunger, and a connection assembly to connect to a suction cannula and a waste assembly. In one aspect, a releasable reservoir, such as a waste collection container, is attached to the handle and trigger assembly. The releasable reservoir allows for the user to discard waste collection containers during a procedure. Proximal movement of the pistol trigger towards the pistol handle is configured to generate a suction force and result in movement of the spring, plunger rod, and plunger within the barrel. Distal movement of the pistol trigger away from the pistol handle is configured to generate a drive force and result in movement of the spring, plunger rod, and plunger within the barrel in an opposite direction. In this embodiment the device also comprises a filter within a collection or waste container. The filter is to separate blood from the UIM thereby allowing a user to visualize the thrombus captured. If the collection or waste container is made from a clear material, it is possible for the user to visualize the filtered UIM within the collection/waste container in real time to ensure that the material has been properly removed from the patient's body. The filtered bodily fluid collected in the collection or waste container may optionally be reinfused back to the patient.

In yet another embodiment (not shown), the handle and trigger assembly comprise a palm handle section and a plurality of finger support members. The palm handle section is designed to securely fit in the palm of a user's handle, thereby providing stability during use. The plurality of finger support members are configured so a user may securely place their fingers on the support members during use. This embodiment also comprises a barrel, spring, plunger rod, plunger, and a connection assembly to connect to a suction cannula and a waste assembly. Either the palm handle section or the plurality of finger support members are securely connected to the plunger rod. Distal movement of the palm handle section towards the plurality of finger support members is configured to generate a suction force and result in movement of the spring, plunger rod, and plunger within the barrel. Proximal movement of the palm handle section away from plurality of finger support members is configured to generate a drive force and result in movement of the spring, plunger rod, and plunger within the barrel in an opposite direction.

In yet another embodiment (not shown), the handle and trigger assembly comprise a two-piece squeeze assembly comprising a first handle section and a second handle arranged in a hinged connection. The device of this embodiment also comprises a barrel, spring, plunger rod, plunger, and a connection assembly to connect to a suction cannula and a waste assembly. The first handle section and second handle section are securely attached to each other at a pivot point and moved in a hinged relationship relative to each other. Movement of the first handle section toward the second handle section along the single pivot point is configured to generate a suction force and result in movement of the spring, plunger rod, and plunger within the barrel. Movement of the first handle section away from the second handle section is configured to generate a drive force and result in movement of the spring, plunger rod, and plunger within the barrel in an opposite direction.

In yet another embodiment (not shown), the handle and trigger assembly comprise a two-piece lateral squeeze assembly comprising a first handle section and a second handle. This embodiment also comprises a barrel, spring, plunger rod, plunger, and a connection assembly to connect to a suction cannula and a waste assembly. The first handle section and second handle section are configured to be squeezed or otherwise moved in a lateral direction. Lateral movement of the first handle section toward the second handle section is configured to generate a suction force and result in movement of the spring, plunger rod, and plunger within the barrel. Lateral movement of the first handle section away from the second handle section is configured to generate a drive force and result in movement of the spring, plunger rod, and plunger within the barrel in an opposite direction.

In yet another embodiment (not shown), the handle and trigger assembly comprise a two-piece horizontal squeeze assembly comprising a first handle section and a second handle. The device of this embodiment also comprises a barrel, spring, plunger rod, plunger, and a connection assembly to connect to a suction cannula and a waste assembly. The first handle section and/or second handle section are configured to move in a horizontal direction. Horizontal movement of the first handle section toward the second handle section is configured to generate a suction force and result in movement of the spring, plunger rod, and plunger within the barrel. Horizontal movement of the first handle section away from the second handle section is configured to generate a drive force and result in movement of the spring, plunger rod, and plunger within the barrel in an opposite direction.

In one embodiment a secondary device (not shown) is used in combination with the suction cannula to aid in the removal of the UIM. The secondary device comprises an elongated body with an expandable element located at a secondary device distal end. The expandable element comprises either an impermeable member, a permeable member, or a member comprising an impermeable portion and a permeable portion. In one embodiment, the secondary device comprises a guidewire member connected to a distal most of end the secondary device. In this embodiment, the guidewire member aids in advancing the secondary device through or to cross a UIM. In one embodiment the expandable element comprises an inflatable balloon. The balloon may be designed with a specific shape, such as a funnel or cone shape. In another embodiment, the expandable element comprises a self-expanding basket. The metal basket may be made of a metal material including, but not limited to, stainless steel or nitinol. The expandable metal basket comprises a thickness, a pitch, and a length of mesh wires. The thickness, the pitch, and the length of the mesh wires may be designed to control the permeability of the expandable metal basket. For example, in one embodiment the thickness, pitch, and length of the mesh wires of the expandable metal basket are configured such to permit fluid flow through the expandable metal basket distal most end but does not permit UIM to flow therethrough. In another embodiment, the thickness, pitch, and length of the mesh wires of the expandable metal basket are configured such to not permit any fluid flow therethrough, thereby consisting of an impermeable expandable metal basket.

The secondary device is co-axially moveable independently from and within a lumen of the suction cannula. A method of using the secondary cannula of this embodiment comprises co-axially advancing the secondary device distally beyond a distal most end of the suction cannula. The secondary device is then advanced through or crosses the UIM so that the expandable element of the secondary device is positioned distally beyond the UIM. Next, a user expands the expandable element distal end of the secondary device. For example, if the expandable element comprises an inflatable balloon the user may inflate the expandable element; or if the expandable element comprises a self-expandable metal basket the user may advance the metal basket out of an introducer sheath. Once the expandable element is activated and in the expanded state, the suction force of the aspiration system may be activated. While the suction force is active the user may retract or pull the secondary device towards and/or co-axially within a lumen of the suction cannula. As the secondary device is retracted or pulled towards the suction cannula the expandable element is configured to engaged with, entrap, mechanically disrupt, and/or macerate the UIM to aid in the removal of the UIM. For example, if the UIM is adhered to a vessel wall the expandable element may mechanically dislodge the UIM from the vessel wall thereby allowing the suction force of the aspiration device to remove the UIM. In other example, if the UIM is occluding the funnel distal end of the suction cannula the expandable element of the secondary device may mechanically squeeze, macerate, and/or force the UIM into the suction cannula lumen for removal. In another embodiment, if the aspiration system is configured to be used in a procedure located in the arterial vascular system, the expandable element of the secondary device can be used as a distal protection device in place of an intravenous filter (as known in the art). For example, in this embodiment the expandable element is designed to be impermeable to the UIM thereby entrapping or blocking any UIM or unwanted debris that becomes dislodged from the treatment site and prevents this material from flowing downstream by fluid flow to the brain or other critical structures in the body to cause additional complications for the patient.

In another embodiment (not shown), the system includes a shaped navigation balloon to aid in the advancement and placement of the suction cannula, thereby removing the need for the outer sheath. In this embodiment, the system comprises a balloon catheter comprises a shaped navigation balloon at the catheter distal end. In one embodiment, the balloon catheter further comprises a guidewire tip connected to a distal most of the balloon catheter to aid in advancement. In another embodiment, the balloon catheter comprises a lumen size for a guidewire to be co-axially placed therethrough. The shaped navigation balloon comprises a proximal funnel shaped end, an elongated body, and a distal funnel shaped end. The shaped navigation balloon is designed to securely fit within the expanded funnel of the suction cannula and comprise a non-traumatic leading end of the shaped navigation balloon. A method of using the shaped navigation balloon comprises co-axially inserting the balloon catheter into the lumen of the suction cannula and advancing the balloon catheter until the shaped navigation balloon is located within the funnel of the suction cannula. Next, the shaped navigation balloon is inflated thereby expanding the balloon and the funnel of the suction cannula. The balloon catheter and suction cannula are then both advanced through the vasculature together and placed at the treatment site. The non-traumatic leading end of the shaped navigation balloon reduces potential risk of traumatic injury during the advancement and/or placement of the suction cannula. Once the suction cannula is properly placed at the treatment device the shaped navigation balloon is deflated. The user may then either retract and remove the balloon catheter from the vasculature, or the user may advance the balloon catheter (with the shaped navigation balloon still in the deflated position) through and cross the UIM to a position distally beyond the UIM. The shaped navigation balloon is then reinflated and the shaped navigation balloon may be used in a similar manner as the expandable element of the secondary device as described above to aid in the removal of the UIM.

In one embodiment (not shown), the suction cannula comprises a suction cannula hub including a suction cannula hub rib, and the outer sheath comprises a hub including an outer sheath hub rib. The suction cannula hub rib is designed to align with a pre-formed bend or shape in the suction cannula along a same longitudinal axis 5. The outer sheath hub rib is designed to align with a pre-formed bend or shape in the outer sheath along a same longitudinal axis 5. The purpose of the suction cannula hub rib is to provide the user with visual feedback on the direction of pre-formed bend or shape in the suction cannula. The purpose of the outer sheath hub rib is to provide the user with visual feedback on the direction of pre-formed bend or shape in the outer sheath. For example, in one embodiment the user may rotate the suction cannula hub and/or the outer sheath hub until the suction cannula hub rib and the outer sheath rib are aligned along the same axis, thereby providing a visual feedback to the user that the pre-formed bend or shape of the suction cannula and the outer sheath are also similarly aligned along the same axis.

In another embodiment (not shown), instead of a waste assembly attached to the system for the removal and disposable of the UIM and removed bodily fluid, the system comprises a reinfusion assembly to filter the UIM and return the filtered bodily fluid back to the patient. In this embodiment, the reinfusion assembly comprises at least one filter and a reinfusion cannula. The filter is placed in fluid communication between the suction cannula and the reinfusion cannula. The filter will entrap and remove any debris from the UIM thereby filtering the bodily fluid removed from the patient in preparation for reinfusion. In this embodiment, the filter is either directly connected to the waste port or a proximal end of an accessory cannula is attached to the waste port and a distal end of the accessor cannula is attached to a first side of the filter. A proximal end of the reinfusion cannula is attached to a second side of the filter. A distal end of the reinfusion cannula is placed in the vasculature of the patient in a manner configured to reinfuse or return the filtered bodily fluid back to the patient. An advantage of this embodiment is that the system may continuously and simultaneously aspirate, filter, and reinfuse the filtered bodily fluid back into the patient, thereby minimize or reduce a risk for any occurrences of fluid loss and/or shock. Also, because the filtered blood is simultaneously and continuously reinfused back to the patient the risks associated with removing more than the total recommended volume of blood in a single procedure (as described above) are minimized.

In another embodiment (not shown), the reinfusion system comprises a blood cell saver. In this embodiment, the blood cell saver is in fluid communication with the suction cannula, aspiration device, and the reinfusion cannula. The blood cell saver is used to filter blood and/or bodily fluid and properly save the blood and/or bodily fluid in case the patient requires a transfusion during and/or after the procedure.

In yet another embodiment (not shown), the reinfusion system comprises an extracorporeal membrane oxygenation (ECMO) device. In this embodiment, the ECMO device is in fluid communication with the suction cannula, aspiration device, and the reinfusion cannula. In this embodiment, if the system is used for treatment of a pulmonary embolism, the ECMO device will maintain proper pressure between the left ventricle and the right ventricle. A known complication for treating pulmonary embolisms is when the suction cannula is inserted into the patient's heart there is a pressure drop in the right ventricle. The reinfusion system of this embodiment solves this problem in the art as the ECMO device may oxygenate the filtered blood before it is reinfused to the patient, thereby helping the right ventricle maintain sufficient pressure.

What is claimed:

1. A device to remove an undesirable material from a vessel, the device comprising:
   a handle body, a trigger assembly, a plunger body, a plunger rod, a barrel, and a connection assembly; the trigger assembly is connected to a proximal end of the plunger rod; a distal end of the handle body is connected to a proximal end of the barrel;
   the connection assembly comprising a barrel inlet channel, a waste port channel, an inlet valve, outlet valve, an inlet connector to be operatively coupled to a suction cannula, and an outlet connector to be operatively coupled to a waste assembly; wherein the connection assembly is connected to a distal end of the barrel;
   wherein at least a section of the plunger rod and the plunger assembly body are co-axially positioned within the barrel;
   wherein the handle body comprises an upper slot, a volume limiter assembly, a vacuum locking mechanism, and a lower slot; and
   wherein the trigger assembly further comprises an upper tab and a lower tab; and wherein the upper tab is configured to slidably move within the upper slot and the lower tab is configured to slidably move within the lower slot.

2. The device of claim 1, wherein a suction cannula lumen, the barrel inlet channel, the inlet valve, a cavity of the barrel, the waste port channel, and the waste assembly are all in fluid communication.

3. The device of claim 1, wherein the volume limiter assembly comprises a first volume setting corresponding to a first volume and a second volume setting corresponding to a second volume; wherein the first volume is less than the second volume; and wherein the volume limiter assembly is configured to engage with the upper tab.

4. The device of claim 1, wherein the inlet valve further comprises an inlet one-way valve, and the outlet valve comprises an outlet one-way valve; and wherein the inlet one-way valve is orientated in an opposite direction to the outlet one-way valve.

5. The device of claim 1, wherein the vacuum locking mechanism is configured to engage with the upper tab to lock the trigger assembly in an aspiration position.

6. The device of claim 1, wherein movement of the trigger in a first direction is configured to generate a suction force through the barrel inlet channel, the inlet valve, and a cavity of the barrel; and wherein movement of the trigger in a second direction is configured to generate a drive force through the waste port channel, the outlet valve, and the cavity of the barrel.

7. The device of claim 6, wherein the vacuum locking mechanism comprises an engaged position and a disengaged position; wherein when the vacuum locking mechanism is in the engaged position the vacuum locking mechanism is configured to limit the movement of the trigger assembly such that the device continuously generates the suction force.

8. The device of claim 4, wherein both the inlet one-way valve and outlet one-way valve are configured to allow the undesirable material to pass through substantially en bloc.

* * * * *